United States Patent
Yue et al.

(10) Patent No.: US 10,435,741 B2
(45) Date of Patent: Oct. 8, 2019

(54) COMPOUNDS AND SYSTEMS FOR IMPROVING SIGNAL DETECTION

(71) Applicant: Pacific Biosciences of California, Inc., Menlo Park, CA (US)

(72) Inventors: Stephen Yue, Eugene, OR (US); Andrei Fedorov, San Bruno, CA (US); Gene Shen, Santa Clara, CA (US); Sophia Wu, Burlingame, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/356,366

(22) Filed: Nov. 18, 2016

(65) Prior Publication Data

US 2017/0145494 A1 May 25, 2017

Related U.S. Application Data

(60) Provisional application No. 62/257,581, filed on Nov. 19, 2015.

(51) Int. Cl.
| | | |
|---|---|---|
| *C12Q 1/6869* | (2018.01) | |
| *C12Q 1/682* | (2018.01) | |
| *G01N 21/64* | (2006.01) | |
| *C12Q 1/6816* | (2018.01) | |
| *C09B 29/00* | (2006.01) | |

(52) U.S. Cl.
CPC ............ *C12Q 1/6869* (2013.01); *C09B 29/00* (2013.01); *C12Q 1/682* (2013.01); *C12Q 1/6816* (2013.01); *G01N 21/6428* (2013.01); *G01N 2021/6439* (2013.01)

(58) Field of Classification Search
CPC .... C12Q 1/6816; C12Q 1/682; C12Q 1/6869; C12Q 2563/107; G01N 2021/6439; G01N 21/6428
See application file for complete search history.

(56) References Cited

U.S. PATENT DOCUMENTS

| | | |
|---|---|---|
| 5,674,716 A | 10/1997 | Tabor et al. |
| 7,993,895 B2 | 8/2011 | Eid et al. |
| 7,998,717 B2 | 8/2011 | Eid et al. |
| 8,071,346 B2 | 12/2011 | Eid et al. |
| 8,586,718 B2 | 11/2013 | Benson et al. |
| 2008/0241892 A1 | 10/2008 | Roitman et al. |
| 2009/0325260 A1 | 12/2009 | Otto et al. |
| 2010/0003765 A1 | 1/2010 | Dixon et al. |
| 2010/0136592 A1 | 6/2010 | Kong et al. |
| 2011/0160077 A1* | 6/2011 | Chaisson ............ C12Q 1/6869 506/9 |
| 2012/0052488 A1 | 3/2012 | Yue et al. |
| 2014/0093935 A1 | 4/2014 | Shen et al. |
| 2015/0125854 A1 | 5/2015 | Fedorov et al. |

OTHER PUBLICATIONS

International Search Report and Written Opinion dated Mar. 3, 2017 for related PCT/US2016/062932.
Johansson et al., "BTI1, an Azoreductase with pH Dependent Substrate Specificity," Appl. Environ. Microbiol. (2011) doi:10.1128/AEM.02289-10.
International Preliminary Report on Patentability dated May 31, 2018 for related PCT/US2016/062932.

* cited by examiner

*Primary Examiner* — Addison D Ault
(74) *Attorney, Agent, or Firm* — David C. Scherer

(57) ABSTRACT

Compositions, devices, systems and methods for increasing the signal to noise ratio (SNR) and/or enhancing photoprotection in an illuminated analytical reaction by addition of one or more signal detection assay (SDA)-enhancing agents to the reaction mixture.

18 Claims, 8 Drawing Sheets

COMPOUNDS AND SYSTEMS FOR IMPROVING SIGNAL DETECTION

CROSS-REFERENCE TO RELATED APPLICATIONS

This application claims the benefit of priority to U.S. Provisional Patent Application 62/257,581 filed Nov. 19, 2015, entitled "Compounds and Systems for Improving Signal Detection", which is hereby incorporated by reference herein in its entirety.

BACKGROUND OF THE INVENTION

The use of optically detectable labeling groups, and particularly those groups having high quantum yields, e.g., fluorescent, phosphorescent, luminescent or chemiluminescent groups, is ubiquitous throughout the fields of analytical chemistry, biochemistry, and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

For example, fluorescence-based optical assays utilizing fluorescent dye labels are frequently used in scientific analyses. The fluorescence detected in a fluorescence-based optical assay is the result of a three-stage process that occurs in the fluorophores or fluorescent dyes present in a reaction mixture. The first stage is excitation in which a photon with quantized energy from an external light source having a specific wavelength (e.g., from a laser) is supplied and absorbed by a fluorophore creating an excited electronic singlet state ($S_1'$). The second stage is the excited-state lifetime in which the excited fluorophore undergoes several different changes to relax its energy to the lowest singlet state ($S_1$). From the $S_1$ state several possible mechanisms can occur in the third stage, fluorescence, in which a photon of energy ($S_1$-$S_0$) is emitted returning the fluorophore to its ground state. Many thousands of these three-stage processes of excitation and emission typically occur to produce a signal detectable by standard optical sensors.

One of the many pathways that dissipate the energy of the excited electronic singlet state is the intersystem crossing (ISC), involving a change in spin multiplicity, transiting the electron from S1 to the excited triplet state (T1). In many fluorescent dye molecules the formation of the much longer life-time triplet-state species greatly reduced the brightness of the fluorescence emission. In addition, it exhibits a high degree of chemical reactivity in this state, which often results in photobleaching and the production of damaging free radicals.

Analyses using optically detectable labeling groups have generally been performed under conditions where the amounts of reactants are present far in excess of what is required for the reaction in question. The result of this excess is to provide ample detectability, as well as to compensate for any damage caused by the detection system and allow for signal detection with minimal impact on the reactants. For example, analyses based on fluorescent labeling groups generally require the use of an excitation radiation source directed at the reaction mixture to excite the fluorescent labeling group, which is then separately detectable. However, one drawback to the use of optically detectable labeling groups is that prolonged exposure of chemical and biochemical reactants to such light sources, alone, or when in the presence of other components, e.g., the fluorescent groups, can damage such reactants, e.g., proteins, enzymes, and the like. The traditional solution to this drawback is to have the reactants present so far in excess that the number of undamaged reactant molecules far outnumbers the damaged reactant molecules, thus minimizing or negating the effects of the photo-induced damage.

A variety of analytical techniques currently being explored deviate from the traditional techniques. In particular, many reactions are based on increasingly smaller amounts of reagents, e.g., in microfluidic or nanofluidic reaction vessels or channels, or in "single molecule" analyses. These analytic systems provide for the observation of only one or a few "events" at a time. For example, such events could be the binding of an antigen to an antibody, a ligand binding to a receptor, cleavage of a polymer (e.g., nucleic acid, protein, or saccharide polymer), incorporation of a unit into a polymer (e.g., an amino acid into a protein, a nucleotide into a nucleic acid, etc.). Such low reactant volumes are increasingly important in many high throughput applications, such they can provide data that is not attainable when observing a plurality of molecules in the more traditional ensemble approaches.

One challenge in performing single-molecule (or few-molecule) reactions comprising labeled reactants is being able to distinguish a labeled reactant engaged in an event under observation from other labeled reactants that are free in the reaction mixture. This is especially important for intermolecular events that require high concentrations of reactants, e.g., to ensure adequate binding to an enzyme catalyzing the reaction. As such, the labeled reactants in the reaction mixture can emit "background" noise that obscures detection of a signal from the event of interest in the reaction mixture. In such analyses, the term "signal-to-noise ratio" refers to a measure that compares the level of a desired signal ("signal") to the level of background signal, or "noise."

Another challenge in performing reactions based upon increasingly smaller amounts of reagents is that such reactions are more severely impacted by photo-induced damage (e.g., photobleaching and free radical formation). For example, photo-induced damage of the enzyme component in a single molecule reaction can completely stop the reaction and prevent further data acquisition.

As such, the present disclosure is directed, inter alia, to methods and compositions that result in (i) an increased signal-to-noise ratio (SNR) in a reaction mixture; (ii) increased photoprotection, or both during illuminated reactions. Increases in SNR can facilitate the detection of reactants when they are participating in an event under observation, e.g., at a reaction site, and thus provide useful improvements to the methods and compositions currently available. For example, methods and compositions that increase the signal-to-noise ratio would not only enhance detection of signals of interest, but could also allow higher concentrations of reactants in various analytical systems. Increased photoprotection in illuminated reactions can enhance the detection of signals of interest and allow reactions to progress for longer periods of time or under more intense illumination conditions, thereby increasing data acquisition and/or allowing higher intensity illumination signals to be employed. These improvements in SNR and photoprotection can lead to increased accuracy in signal detection assays, e.g., single-molecule sequencing reactions.

BRIEF SUMMARY OF THE INVENTION

The present invention is generally directed to compounds, compositions, methods, devices and systems for improving signal detection assays in illuminated reactions by (i) increasing the signal-to-noise ratio (SNR), (ii) enhancing photoprotection, or both in illuminated reactions. The term "illuminated reaction" as used herein refers to reactions which are exposed to an optical energy source. Typically, such illumination is provided in order to observe the generation and/or consumption of reactants or products that possess a particular optical characteristic indicative of their presence, such as an alteration (in intensity, wavelength, etc.) in the absorbance spectrum and/or emission spectrum of the reaction mixture or its components.

Increasing the SNR may be achieved by reducing or limiting the effects of background noise and/or enhancing one or more optical signal being detected during illuminated reactions, particularly reactions that employ fluorescent or fluorogenic reactants. This increased SNR is useful to enhance the detectability of labeled reactants engaged in an observed intermolecular event. Enhancing photoprotection may be achieved by preventing, eliminating, reducing, or limiting (also referred to as "mitigating") the effects of photo-induced damage (PID) to one or more reaction components in the mixture and/or reducing blinking or photobleaching of the optically detectable molecule or moiety, e.g., a fluorescent moiety. Increasing SNR, enhancing photoprotection, or both in illuminated reactions can lead to improvements in the performance of such reactions, e.g., improving the accuracy of fluorescence-based single-molecule sequencing reactions.

In one aspect, the invention provides reaction mixtures that include an optically detectable molecule or moiety and a signal detection assay (SDA)-enhancing agent. An SDA-enhancing agent of the present disclosure (i) increases SNR, (ii) enhances photoprotection, or both, when present at an effective amount in an illuminated reaction. The SDA-enhancing agent can increase SNR by increasing the intensity or strength of the signal(s) to be detected and/or reducing the background noise, resulting in an overall increase to the SNR of the detected signal (e.g., fluorescence) in the illuminated reaction mixture. The SDA-enhancing agent can enhance photoprotection by mitigating the effects of PID to one or more reaction components in the mixture and/or reducing blinking or photobleaching of an optically detectable molecule or moiety (e.g., a fluorescent moiety). In certain embodiments, a single SDA-enhancing agent both increases SNR and enhances photoprotection in an illuminated reaction. The improvements in signal detection in illuminated reactions comprising an SDA-enhancing agent are based on comparisons to control illuminated reactions that lack the SDA-enhancing agent. Thus, a reaction mixture of the invention includes an SDA-enhancing agent that, upon illumination of the reaction mixture: (i) increases an optical signal from an optically detectable molecule or moiety (e.g., increases the brightness of a fluorescent label), (ii) reduces an amount of background noise, (iii) mitigates PID, (iv) reduces blinking or photobleaching, or any combination thereof, including all of (i) to (iv), that would otherwise occur in the absence of the SDA-enhancing agent.

In certain embodiments, the optically detectable molecule or moiety in an illuminated reaction is a fluorescent or fluorogenic molecule or moiety.

In certain embodiments, an SDA-enhancing agent comprises an SDA-enhancing moiety, where the SDA-enhancing moiety comprises an azo group of the formula $R_a$—N=N—$R_b$, where both $R_a$ and $R_b$ comprise an aromatic moiety, and where $R_a$ comprises a hydrophilic moiety, e.g., covalently attached. In certain embodiments, both $R_a$ and $R_b$ comprise a hydrophilic moiety (either the same hydrophilic moiety or different hydrophilic moieties). In certain embodiments, the aromatic moieties of $R_a$ and $R_b$ are the same while in other embodiments, the aromatic moieties are different. In certain embodiments, the aromatic moiety of $R_a$ and $R_b$ are selected from: aryl compounds, heterocyclic aromatic compounds, polycyclic aromatic compounds, and combinations thereof. In certain embodiments, the SDA-enhancing agent comprises an azo-diaryl compound. In certain embodiments, the SDA-enhancing agent has a formula selected from:

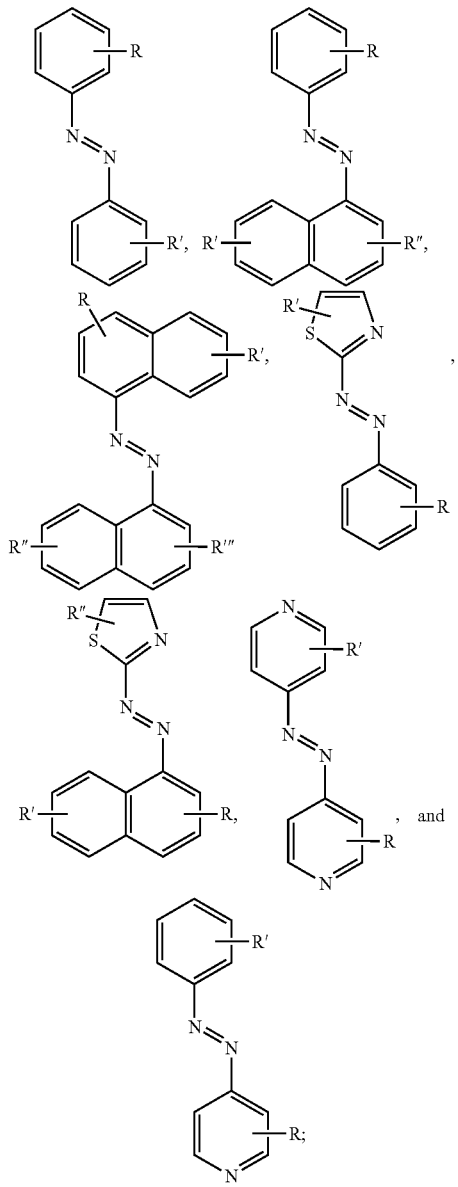

where each SDA-enhancing agent includes at least one R group (one or more of R, R', R", and R'''), and where the at least one R group comprises a hydrophilic moiety. Any hydrophilic moiety is contemplated, where in certain embodiments, the hydrophilic moiety is selected from: sulfonate, carboxylate, phosphate, phosphonate, amide, $NH_2$, $NR''''_2$, OH, N-sulfonylalkyl, O-sulfoalkyl, and combinations thereof. In certain embodiments, a single aromatic group of an SDA-enhancing agent comprises more than one hydrophilic moiety. While not being bound by theory, it appears that the diaromatic-azo moiety functions to increase SNR, enhance photoprotection, or both.

In certain embodiments, the hydrophilic moiety is attached to the SDA-enhancing moiety via a linker.

In certain embodiments, the SDA-enhancing agent has a formula selected from Table 1 below:

TABLE 1

Representative SDA-Enhancing Agents

| SDA-Enhancing Agent No. | Structure |
| --- | --- |
| 1 | 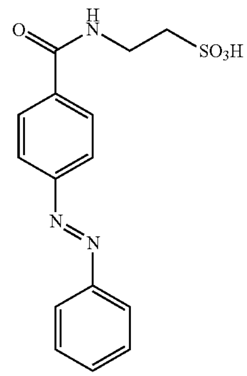 [SMILES: O=C(NCCS(=O)(=O)O)c1ccc(/N=N/c2ccccc2)cc1] |
| 2 | 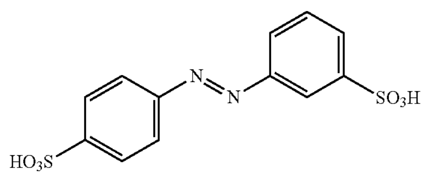 [SMILES: O=S(=O)(O)c1ccc(/N=N/c2cccc(S(=O)(=O)O)c2)cc1] |
| 3 | |
| 4 | 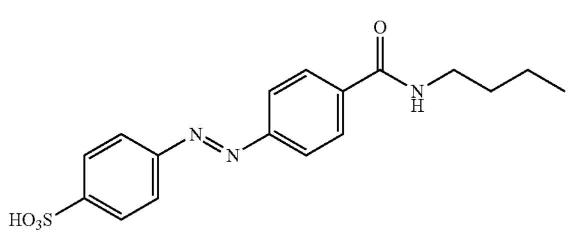 [SMILES: CCCCNC(=O)c1ccc(/N=N/c2ccc(S(=O)(=O)O)cc2)cc1] |

TABLE 1-continued

Representative SDA-Enhancing Agents

| SDA-Enhancing Agent No. | Structure |
| --- | --- |
| 5 | 4-((4-((6-(5-((3aS,4S,6aR)-2-oxohexahydro-1H-thieno[3,4-d]imidazol-4-yl)pentanamido)hexyl)carbamoyl)phenyl)diazenyl)benzenesulfonic acid |
| 6 | 4,4'-(diazene-1,2-diyl)bis(N-(2-sulfoethyl)benzamide) |
| 7 | Potassium 2-((2-(4-hydroxyphenyl)diazenyl)benzoate |
| 8 | Potassium 4-(phenyldiazenyl)benzoate |
| 9 | Triethylammonium 4-((3-sulfophenyl)diazenyl)benzoate |

TABLE 1-continued
Representative SDA-Enhancing Agents
| SDA-Enhancing Agent No. | Structure |
|---|---|
| 10 | 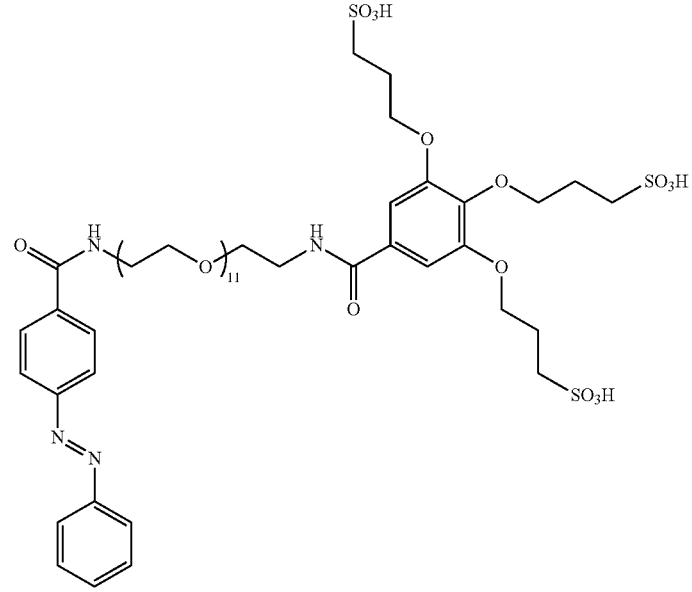 |
| 11 | 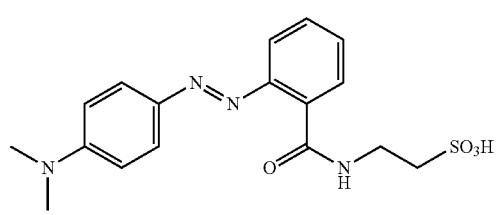 [SMILES: CN(C)c1ccc(/N=N/c2ccccc2C(=O)NCCS(=O)(=O)O)cc1] |
| 12 | 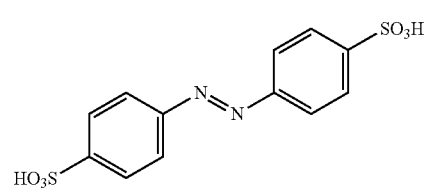 [SMILES: O=S(=O)(O)c1ccc(/N=N/c2ccc(S(=O)(=O)O)cc2)cc1] |
| 13 | 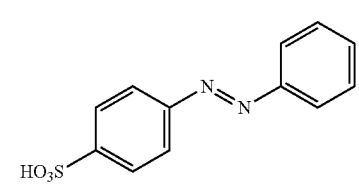 [SMILES: O=S(=O)(O)c1ccc(/N=N/c2ccccc2)cc1] |
| 14 | 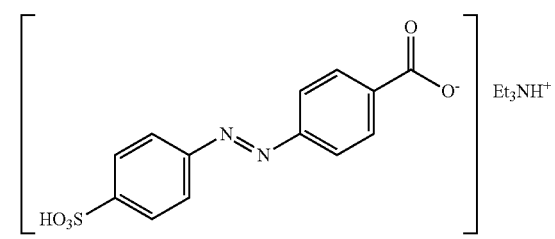 |

TABLE 1-continued

Representative SDA-Enhancing Agents

| SDA-Enhancing Agent No. | Structure |
|---|---|
| 15 | 4-((4-(N-(4,4,4-trifluorobutyl)carbamoyl)phenyl)diazenyl)benzenesulfonic acid |
| 16 | 4,4'-(diazene-1,2-diyl)dibenzoic acid |
| 17 | PEG-linked phenyldiazenyl benzamide with terminal carboxylic acid |
| 18 | Sulfoethyl-amide and butyl-amide substituted azobenzene dicarboxamide |
| 29 | 4-((4-(N-(2-sulfoethyl)carbamoyl)phenyl)diazenyl)benzoic acid |
| 20 | Phenyldiazenyl benzamide-hexanamide-sulfoethyl conjugate |

TABLE 1-continued

Representative SDA-Enhancing Agents

| SDA-Enhancing Agent No. | Structure |
| --- | --- |
| 21 | 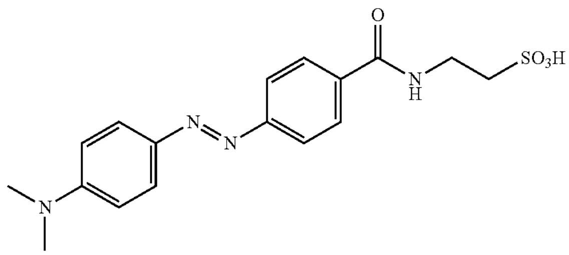 [SMILES: CN(C)c1ccc(/N=N/c2ccc(C(=O)NCCS(=O)(=O)O)cc2)cc1] |
| 22 | 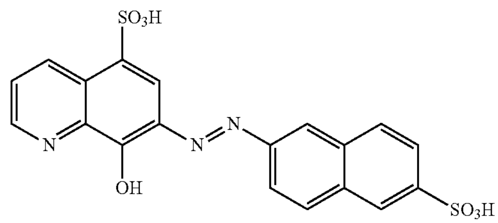 [SMILES: O=S(=O)(O)c1ccc2cc(/N=N/c3cc(S(=O)(=O)O)c4cccnc4c3O)ccc2c1] |
| 23 | 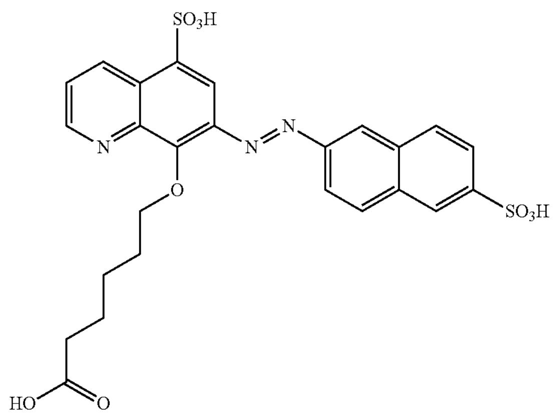 [SMILES: O=C(O)CCCCCOc1c(/N=N/c2ccc3cc(S(=O)(=O)O)ccc3c2)cc(S(=O)(=O)O)c2cccnc12] |
| 24 | 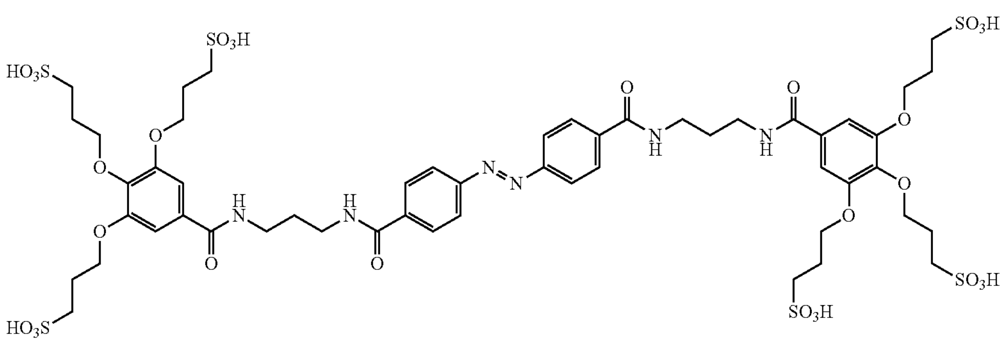 [SMILES: O=C(NCCCNC(=O)c1cc(OCCCS(=O)(=O)O)c(OCCCS(=O)(=O)O)c(OCCCS(=O)(=O)O)c1)c1ccc(/N=N/c2ccc(C(=O)NCCCNC(=O)c3cc(OCCCS(=O)(=O)O)c(OCCCS(=O)(=O)O)c(OCCCS(=O)(=O)O)c3)cc2)cc1] |
| 25 | 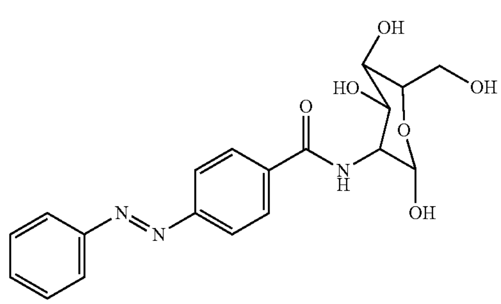 [SMILES: O=C(NC1C(O)OC(CO)C(O)C1O)c1ccc(/N=N/c2ccccc2)cc1] |

TABLE 1-continued

Representative SDA-Enhancing Agents

| SDA-Enhancing Agent No. | Structure |
|---|---|
| 26 | [chemical structure: 4-boronic acid phenyl azo 3-sulfonic acid phenyl] |
| 27 | [chemical structure: azo compound with HO₃S-phenyl, hydroxyl, and propoxy-sulfonate substituents] |
| 28 | [chemical structure: bis-azo bis-benzamide ethylenediamine with taurine-like sulfonate termini] |

In some embodiments, included in a reaction mixture is a nucleoside polyphosphate (or analog thereof) and/or an enzyme, e.g., a polymerase, helicase, exonuclease, ribosome, or ligase enzyme. The mixture can further include a template nucleic acid molecule. At least one component of the reaction mixture can be confined within an optical or structural confinement, e.g., a zero-mode waveguide, nanopore, micro- or nanochannel, etc. In certain embodiments, at least one component of the reaction mixture is linked to a fluorescent or fluorogenic molecule. In certain specific embodiments, a component of the reaction mixture comprising a fluorescent label is an enzyme, nucleotide polyphosphate, polynucleotide, tRNA, amino acid, or analog thereof.

In another aspect, the present disclosure provides methods for improving signal detection in an illuminated reaction, the methods including obtaining a reaction mixture comprising an SDA-enhancing agent, illuminating the reaction mixture with excitation illumination, and detecting a signal from the illuminated reaction mixture. The SDA-enhancing agent increases the SNR and/or enhances photoprotection in the reaction mixture as compared to the same reaction mixture in the absence of the SDA-enhancing agent. As such, in certain embodiments, the SNR is increased to a level greater than the SNR in the absence of the SDA-enhancing agent by increasing the brightness of the signal to a level that is greater than the brightness of the signal in the absence of the SNR-enhancing agent and/or reducing an amount of background noise to an amount that is less than that which would occur in the absence of the SDA-enhancing agent. In further embodiments, the SDA-enhancing agent has a photoprotective activity in the illumination reaction by mitigating PID to a component in the reaction mixture (e.g., an enzyme) and/or reducing blinking or photobleaching of a fluorescent label, or both, as compared to the same illumination reaction in the absence of the SDA-enhancing agent. Thus, in certain embodiments, inclusion of an SDA-enhancing agent comprising a photoprotective moiety can increase the PID threshold period for an illuminated reaction (i.e., the amount of time an illuminated analysis may be carried out before PID so substantially impacts the reactants to render the analysis non-useful), allowing an increased amount of data to be collected from a reaction. Where the method is a method of sequencing a polynucleotide, the SNR-enhancing and photoprotective effects of the SDA-enhancing agent increases the sequencing accuracy of the reaction.

In certain embodiments, methods of the invention further include the step of monitoring a reaction between an enzyme and a fluorescent or fluorogenic substrate while illuminating the reaction mixture. In some preferred embodiments, the illuminated reaction is a base extension reaction and the enzyme is optionally a polymerase. Such a reaction typically includes at least one polynucleotide (e.g., template) and a plurality of nucleotide polyphosphates. In other preferred embodiments, the illuminated reaction is a translation reaction during which a polypeptide is synthesized. Such a reaction typically includes a ribosome, and mRNA, and a plurality of amino acid-charged tRNAs. Preferably, one or more component of the reaction mixture are confined upon a substrate, e.g., within a zero-mode waveguide or a microfluidic channel, or near/within a nanopore.

In a further aspect, the present invention provides methods for preparing an illuminated reaction mixture (e.g., a sequencing or base-extension reaction mixture) that comprises fluorescent of fluorogenic compounds. The methods include adding an SDA-enhancing agent described herein (see description of SDA-enhancing agents above) to the reaction mixture, the SDA-enhancing agent including an SNR-enhancing moiety, a photoprotective moiety, or both.

In another aspect, the present invention provides methods for increasing the accuracy of an illuminated sequencing reaction and/or obtaining more sequencing data from an illuminated sequencing reaction. The methods include providing a reaction mixture that includes a polymerase, a template nucleic acid, one or more fluorescent or fluorogenic nucleotides or nucleotide analogs, and an SDA-enhancing agent (as described in detail herein). The reaction mixture is exposed to excitation illumination and emission signals are detected from the reaction mixture, e.g., during monitoring of the reaction mixture during the exposure to excitation illumination. In certain embodiments, the presence of the SDA-enhancing agent enhances the accurate detection of the fluorescent or fluorogenic nucleotides, thereby increasing the accuracy of the resulting sequencing reaction data. For example, the SDA-enhancing agent can (i) decrease an amount of background noise and/or increase the strength of the signal being detected, (ii) enhance photoprotection, or both, where the enhancements to the illuminated reaction are as compared to the same reaction without the SDA-enhancing agent. In certain preferred embodiments, the illuminated sequencing reaction is a base extension reaction, e.g., a template-directed nascent strand extension reaction. Optionally, at least one component of the reaction mixture (e.g., the polymerase or the template nucleic acid) is confined at a reaction site, e.g., within a zero-mode waveguide, at or proximal to a nanopore, or within a microfluidic channel.

In certain aspects, the invention provides a method for increasing SNR and/or enhancing photoprotection in an illuminated reaction. In preferred embodiments, the method comprises providing a reaction mixture comprising a fluorescent or fluorogenic reactant and an unlabeled reactant, wherein the unlabeled reactant is immobilized at a reaction site; adding an SDA-enhancing agent to the reaction mixture, wherein the SDA-enhancing agent comprises an SDA-enhancing moiety and a hydrophilic moiety (as described herein); and illuminating the reaction mixture with an excitation illumination. In certain embodiments, as noted above, the SDA-enhancing moiety can be linked to the hydrophilic moiety via a linker. The SDA-enhancing agent can (i) reduce an amount of background noise to an amount that is less than that which would occur in the absence of the SDA-enhancing agent, (ii) increase the intensity of a signal detected from the reaction mixture to a level that is more than that which would occur in the absence of the SDA-enhancing agent, (iii) mitigate PID to an unlabeled reactant resulting from interaction of the unlabeled reactant with the fluorescent or fluorogenic reactant under the excitation illumination as compared to the same reaction without the SDA-enhancing agent, and/or (iv) reduce blinking or photobleaching of the fluorescent of fluorogenic reactant as compared to the same reaction without the SDA-enhancing agent. In some embodiments, the unlabeled reactant is an enzyme, e.g., a polymerase, helicase, exonuclease, or a ligase. In some embodiments, the illuminated reaction is a base extension or sequencing-by-synthesis reaction. In some embodiments, the illuminated reaction comprises passage of the fluorescent or fluorogenic reactant near or through a nanopore, nanochannel, or microchannel. In certain embodiments, the illuminated reaction takes place in a confined reaction site, e.g., near or within a nanopore or zero-mode waveguide. In preferred embodiments, the fluorescent or fluorogenic reactant comprises a nucleoside polyphosphate or analog thereof. The method can further comprise monitoring a reaction between the fluorescent or fluorogenic reactant and the unlabeled reactant while illuminating the reaction mixture.

The present invention also provides kits that incorporate SDA-enhancing agents, or admixtures thereof, optionally with additional useful reagents. Such kits typically include a SDA-enhancing agent of the invention packaged in a fashion to enable use of the agent with any of a variety of analytical reaction components that participate in a reaction with one or more fluorescent or fluorogenic reaction components. For example, a SDA-enhancing agent of the invention can be packaged with any of a variety of enzymes that participate in a reaction with one or more fluorescent or fluorogenic substrates. Alternatively, a SDA-enhancing agent of the invention can be packaged with any of a variety of antibodies that participate in a reaction with one or more fluorescent or fluorogenic antigens, or vice versa. In still other embodiments, a SDA-enhancing agent of the invention can be packaged with any of a variety of protein receptors that participate in a reaction with one or more fluorescent or fluorogenic ligands. It will be clear that the methods, compositions, and systems described herein are useful with a multitude of other types of analytical reactions, including but not limited to hybridization assays, binding assays (e.g., antibody assays), nucleic acid sequencing assays, protein sequencing assays, polymerization assays, ligation reactions, catalytic reactions, etc. Depending upon the desired application, the kits of the invention optionally include, e.g., buffer solutions and/or salt solutions, divalent metal ions, i.e., $Mg^{++}$, $Mn^{++}$, $Ca^{++}$, $Zn^{++}$ and/or $Fe^{++}$, enzyme cofactors, substrates, standard solutions, e.g., dye standards for detector calibration, etc. Kits can optionally include reagents and instructions for preparing SDA-enhancing agent admixtures. Such kits also typically include instructions for use of the compounds and other reagents in accordance with the desired application methods, e.g., nucleic acid sequencing and the like.

DETAILED DESCRIPTION OF THE INVENTION

Figure 1:
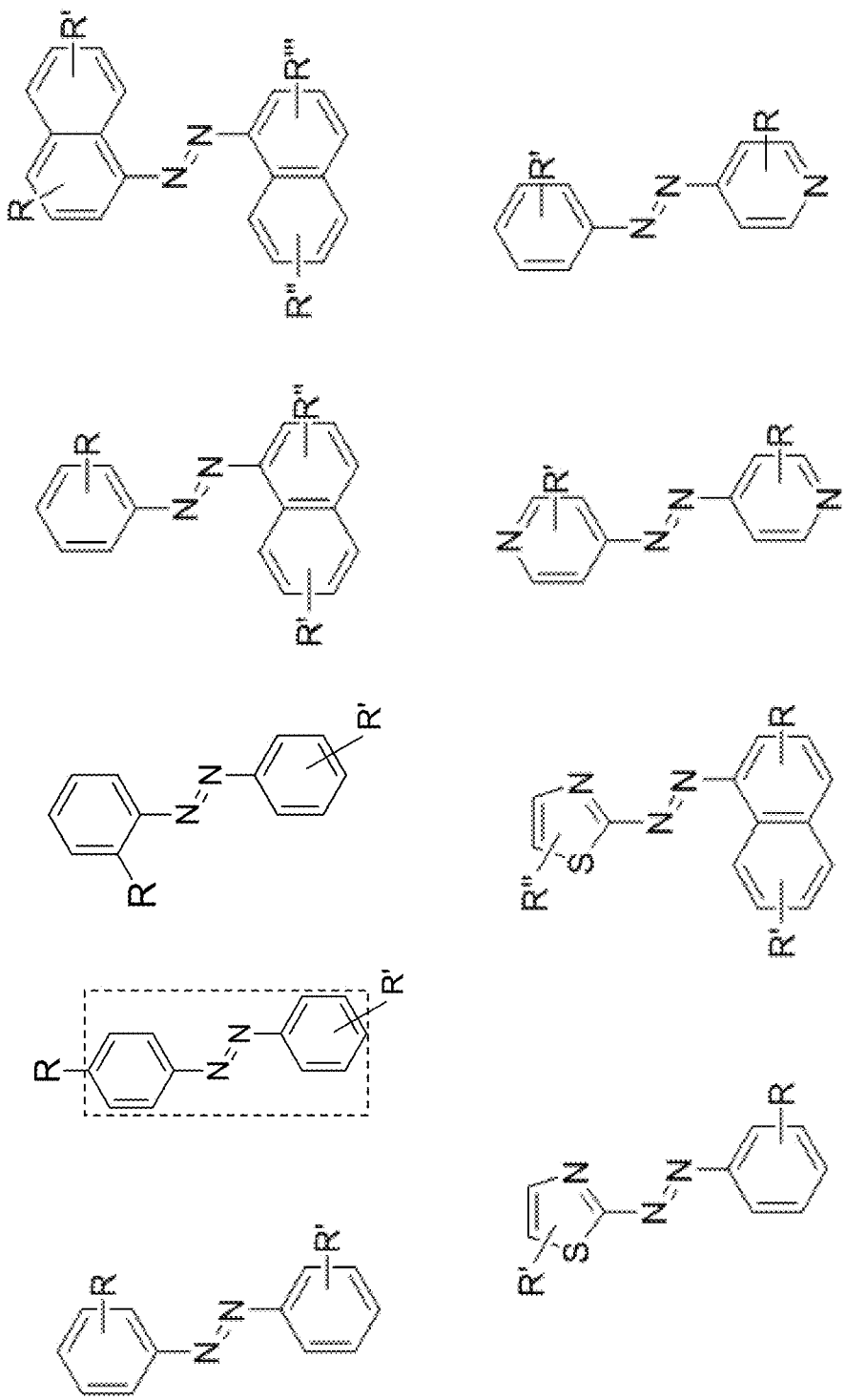
FIG. 1 is a schematic illustration of various generic structures of SDA-enhancing agents.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

I. General

The present invention is generally directed to compounds, compositions, methods, devices and systems for improving signal detection assays in illuminated reactions by employing SDA-enhancing agents that (i) increase the signal-to-noise ratio (SNR), (ii) enhance photoprotection, or both in illuminated reactions, particularly reactions that employ fluorescent or fluorogenic reactants. Fluorescent or fluorogenic reactants generally include reaction components linked to a fluorescent or fluorogenic molecule or "label." Such reaction components include without limitation enzymes, enzyme substrates, cofactors, reactive proteins, binding partners, ligands, and other types of molecules desired to be detected during an analytical reaction. Further, in some embodiments, a fluorescent or fluorogenic molecule can be linked to a reaction site rather than, or in addition to, a reaction component. The present invention provides methods and compositions for improving illuminated reactions by (i) reducing an amount of background noise to an amount that is less than that which would occur in the absence of the SDA-enhancing agent, (ii) increasing the intensity of a signal detected from the reaction mixture to a level that is more than that which would occur in the absence of the SDA-enhancing agent, (iii) mitigating PID to an unlabeled reactant as compared to the same reaction without the SDA-enhancing agent, and/or (iv) reducing blinking or photobleaching of the detectable moiety as compared to the same reaction without the SDA-enhancing agent. The term "illuminated reactions" as used herein refers to reactions which are exposed to an optical energy source.

Typically in an illuminated reaction, illumination is provided in order to observe the presence (e.g., generation, binding, activity, and/or consumption) of reactants or products that possess a particular optical characteristic indicative of their presence, such as a shift in the absorbance spectrum and/or emission spectrum of the reaction mixture or its components, or a change in intensity of fluorescence, e.g., at a reaction site. Signals of interest are detected that inform about reaction events. The ability to detect these informational signals is affected by the amount of background noise that is also being detected. If the noise is too high, the signal becomes swamped out and is difficult, if not impossible, to detect.

Certain illumination reactions detect fluorescence of one or more fluorescently labeled reactants. Fluorescence detected in such fluorescence-based optical assays is the result of a three-stage process that occurs in the fluorophores or fluorescent dyes present in a reaction mixture. The first stage is excitation in which a photon with quantized energy from an external light source having a specific wavelength (e.g., from a laser) is supplied and absorbed by a fluorophore creating an excited electronic singlet state ($S_1'$). The second stage is the excited-state lifetime in which the excited fluorophore undergoes several different changes to relax its energy to the lowest singlet state ($S_1$). From the $S_1$ state several possible mechanisms can occur in the third stage, fluorescence, in which a photon of energy ($S_1$-$S_0$) is emitted returning the fluorophore to its ground state. Many thousands of these three-stage processes of excitation and emission typically occur to produce a signal detectable by standard optical sensors.

One of the many pathways that dissipate the energy of the excited electronic singlet state ($S_1$) is the intersystem crossing (ISC), which involves a change in spin multiplicity that transits the system from $S_1$ to the excited triplet state ($T_1$). In many fluorescent dye molecules, the formation of the much longer lifetime triplet-state species competes with fluorescence emission and greatly reduces the brightness of the fluorescence emission. In addition, fluorescent dyes exhibit a high degree of chemical reactivity in this state that often results in photobleaching and the production of damaging free radicals and reactive intermediates, e.g., radical ions, carbenes, carbocations, carbanions, etc. Further, there is also evidence to suggest that even a fluorophore in the $S_1$ state can react with reaction components, e.g., negatively impacting an analytical reaction by mediating the production of non-reactive intermediates.

One object of the invention is to increase the signal-to-noise ratio, also termed SNR, which is a measure that compares the level of a desired signal ("signal") to the level of background signal, or "noise." It is defined as the ratio of signal power to the noise power. If the background noise is too high, e.g., approaching the level of the signals, the signals may not be detectable over the noise. Although background noise is sometimes referred to as "background signal" in the art, herein it will generally be referred to as "noise," "background," or "baseline" to distinguish it from the signals that one wishes to detect during an analysis, which are typically signals that inform about an analytical process. For example, if the analytical process is a sequencing reaction, the signals that inform about the process would include signals that identify nucleotides in the template nucleic acid being sequenced. Similarly, if the analytical process is a binding reaction, the signals that inform about the process would include signals indicative of a binding event.

There are various strategies for improving the SNR in an analytical assay. One approach for increasing the SNR so a signal can be detected over the noise is to increase the brightness (also generally referred to as "strength" or "intensity") of the signal, but this can also increase the background noise. For example, if a ligand is labeled with a fluorescent dye and placed in a reaction mixture at a concentration appropriate for binding to a receptor, both the freely diffusing labeled ligand and any ligand bound to the receptor will have the same label and, therefore, emit the same signal. As such, if the brightness of the label on the bound ligand is increased, so is the brightness of the background noise. Another approach for increasing the SNR is to reduce the background by removing freely diffusing labeled reagents from the reaction mixture during detection of reagents that are participating in a reaction event. This can be effective where the removal does not disturb the ligand-receptor complexes, but this approach does not work well for assays that are ongoing and require a continual supply of reactants, such as kinetic studies of binding and dissociation over time or ongoing enzymatic reactions, such as sequencing-by-synthesis reactions performed in real time. Yet another approach for increasing the SNR is to reduce the background by reducing the illumination of the reaction mixture as a whole, i.e., illuminating only a portion of the reaction mixture and/or isolating the reaction events from the freely diffusing reagents. In doing so, the labeled reactants in the portion of the reaction mixture that is not being illuminated will not contribute to the background noise. For example, if a location at which a reaction is happening ("a reaction site") is in a confined area such that only a small volume of the reaction mixture is illuminated, most of the freely diffusing reagents will not be illuminated during detection of the reaction events. One or more components of the reaction mixture can be immobilized at the reaction site, so observation is limited to the volume of the reaction mixture around that reaction site and labeled reactants outside the observation volume are not detectable. One example of this strategy is the use of zero-mode waveguides, which greatly limit the observation volume and provide a system for single-molecule detection. Zero-mode waveguides are described in detail in, e.g., U.S. Pat. Nos. 6,917,726, 7,013,054, 7,170,050, 7,315,019, 7,486,865, 7,907,800, and 8,247,216, all of which are incorporated herein by reference in their entireties for all purposes. That will effectively lower the noise that interferes with signal detection, but some freely diffusing reactants may still enter the reaction site and introduce some level of noise. In reactions where the concentration of a labeled ligand or other reactant is high, there may still be enough unbound ligands within the illuminated volume to hamper detection of any that are bound. Reducing the concentration of labeled reactants can help to reduce background noise, but the reduced concentration may also negatively affect the ongoing reaction. Quenching agents can also be used to reduce background noise, but they can also quench the signal being detected so that there is no or a very low net gain in SNR. These various strategies can be used independently or in combination, depending on the specific reaction conditions of the analytical system.

Another object of the invention is directed to improving the performance of illuminated reaction analyses by reducing blinking and/or photobleaching of fluorescent moieties in the reaction and/or mitigating PID to reaction components thereby increasing the amount of time that permits the effective performance of the analysis. In some embodiments, a SDA-enhancing agent prevents, slows, or removes the accumulation of damaging excited triplet-state forms of one or more reaction components. For example, in specific embodiments, using SDA-enhancing agents of the invention slows the accumulation of the excited triplet state of a fluorophore by, e.g., reducing $T_1$ lifetime and restoring the fluorophore to its ground state ($S_0$) (thereby facilitating the availability of the fluorophore to absorb another photon and fluoresce again), greatly improving the photophysical properties of the dye. This reduction in triplet state lifetime also reduces the likelihood that other reaction components will undergo photo-induced damage caused by interaction with a triplet-state dye, thereby essentially protecting the other reaction components and potentially extending the time during which the reaction can generate useful data. These photoprotective effects result in increased performance of illuminated reactions, including increasing the accuracy of sequencing by synthesis reactions, e.g., single-molecule sequencing reactions.

In certain embodiments, the SDA-enhancing agent added to an illumination reaction has both SNR-enhancing and photoprotective activities.

In general terms, the invention is directed to the performance of illuminated analytical assays, where such assays are carried out in a manner that permits the effective performance of the analysis. For example, the analysis should not be impeded by suboptimal concentrations of the reactants. Further, the signals from the analysis that are indicative of the progress of the reaction should be readily distinguishable from background noise emanating from reactants that are free in the reaction mix and not actively engaging in a reaction event. It will be understood that although such assays are sometimes referred to as "reactions" or "analytical reactions" that are performed using "reaction mixtures" comprising components called "reactants," these terms do not necessarily imply a chemical reaction is taking place. For example, a binding event can be considered a reaction even where the binding partners (reactants) are not chemically changed. Likewise, detection during passage into or through a microchannel, nanopore, or other restricted space can also be referred to as an analytic reaction.

In certain aspects, the invention provides a set of additives, termed "SDA-enhancing agents," that have been shown to have an unexpected effect on the increasing the SNR of illuminated reactions, enhancing photoprotection, or both.

In certain embodiments, these additives can decrease background noise in these reactions and can also increase the brightness of the signal to be detected, thereby enhancing the SNR of the reaction in two different ways. This combination of signal enhancement and noise reduction by a single molecule is very different from the conventional SNR-enhancing strategies discussed above, and provides a distinct improvement over methods that only focus on one aspect of the SNR challenge. The enhancement of SNR provided by these additives allows for easier detection of signals from reaction events in the presence of a high concentration of labeled reactants in a reaction mixture, thereby increasing the efficiency of the reaction and the accuracy of the reaction data being collected and analyzed.

In analyzing SDA-enhancing agents, it was found, unexpectedly, that they also have photoprotective activity in illumination reaction mixtures. This dual activity of the SDA-enhancing agents allowed for significant increases in the accuracy of certain illumination assays (see additional description below and Examples). Without being bound to a particular theory or mechanism of operation, it is believed that several mechanisms, independently or in combination, underlie the effectiveness of these additives.

One mechanism is the reduction of the background noise through collisional quenching between the SDA-enhancing agents and freely diffusing labeled reactants, which leads to a net increase in SNR. Some local binding of the SDA-enhancing agents near the reaction site and/or one or more reagents may also take place. Another mechanism is through energy transfer quenching, a dark quencher mechanism, where there is sufficient overlap between the emission from the labeled reactant and an absorption spectra of the SDA-enhancing agent. A further mechanism is via interaction with a label having multiple dyes, e.g., a FRET dye, optionally having more than one donor fluorophore and/or more than one acceptor fluorophore. Interaction with such multi-dye labels may cause the constituent dyes to align in a conformation that increases the efficiency of excitation, transfer, and emission.

In another mechanism, SDA-enhancing agents can function as triplet-state quenchers and/or free radical quenchers that provide significant photoprotective activity, e.g., to prevent, slow, or remove the accumulation of damaging excited triplet-state forms of one or more reaction components and/or to reduce blinking or photobleaching of fluorescent moieties. Reducing the accumulation of the excited triplet state reduces the likelihood that other reaction components will undergo photo-induced damage caused by interaction with a triplet-state dye. This activity protects the other reaction components and extends the time during which the reaction can generate useful data. Reducing blinking and photobleaching improves fluorescent detection and analysis, especially in illuminated reactions that are monitored over time, e.g., sequencing reactions.

In certain preferred embodiments, the invention provides one or more SDA-enhancing agents that comprise an SDA-enhancing moiety and a hydrophilic moiety (e.g., a positively or negatively charged moiety) to be used as additives in a reaction mixture for use in an illumination reaction. In certain embodiments, the hydrophilic moiety can be directly linked to the SDA-enhancing moiety or can be connected to it through a linker.

Various different types of linkers having different lengths and chemical properties can be used. The term "linker" encompasses any moiety that is useful to connect one or more molecules or compounds (e.g., SDA-enhancing moieties and hydrophilic moieties), e.g., to each other, to other components of a reaction mixture, and/or to a reaction site. For example, a linker can connect an SDA-enhancing agent to a reaction site or a reaction; a linker can attach a reporter molecule or "label" (e.g., a fluorescent dye) to a reaction site or a reaction component (e.g., an enzyme, substrate, ligand, binding partner, etc.); and a linker can covalently link an SNR-enhancing and/or photoprotective moiety to a hydrophilic moiety to form a SDA-enhancing agent. Linkers may also be branched to connect three or more components of a reaction mixture, e.g., in to a tridentate, tetradentate, or higher order structure. Methods for choosing, synthesizing, and attaching linkers to reactants and surfaces are well known to those of ordinary skill in the art and further discussion and exemplary linker moieties are provided, e.g., in U.S. Ser. No. 61/026,992 (filed Feb. 7, 2008), Ser. No. 12/367,411, (filed Feb. 6, 2009), and U.S. Published Patent Application No. 2009/0233302, the disclosures of which are incorporated herein by reference in their entireties for all purposes.

In certain embodiments, the linker is a member selected from substituted or unsubstituted alkyl (e.g., a 2-5 carbon chain), substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker moiety is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl). In certain embodiments, molecules that have trifunctional linkage capability are used, including, but are not limited to, cynuric chloride, mealamine, diaminopropanoic acid, aspartic acid, cysteine, glutamic acid, pyroglutamic acid, S-acetylmercaptosuccinic anhydride, carbobenzoxylysine, histine, lysine, serine, homoserine, tyrosine, piperidinyl-1, 1-amino carboxylic acid, diaminobenzoic acid, etc. In certain specific embodiments, a hydrophilic PEG (polyethylene glycol) linker is used.

In certain embodiments, linkers are derived from molecules which comprise at least two reactive functional groups (e.g., one on each terminus), and these reactive functional groups can react with complementary reactive functional groups on the various reaction components or used to immobilize one or more reaction components at the reaction site. "Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

In general, an SDA-enhancing moiety of an SDA-enhancing agent comprises where the SDA-enhancing moiety comprises an azo group of the formula $R_a$—N═N—$R_b$, where both $R_a$ and $R_b$ comprise an aromatic moiety, and where $R_a$ comprises a hydrophilic moiety. The N═N group is referred to as an azo group. In certain embodiments, both $R_a$ and $R_b$ comprise a hydrophilic moiety (either the same hydrophilic moiety or different hydrophilic moieties). In certain embodiments, the aromatic moieties of $R_a$ and $R_b$ are the same while in other embodiments, the aromatic moieties are different. In certain embodiments, the aromatic moiety of $R_a$ and $R_b$ are selected from: aryl compounds, heterocyclic aromatic compounds, polycyclic aromatic compounds, and combinations thereof. In certain embodiments, the SDA-enhancing agent comprises an azo-diaryl compound. In certain embodiments, the SDA-enhancing agent has formula selected from:

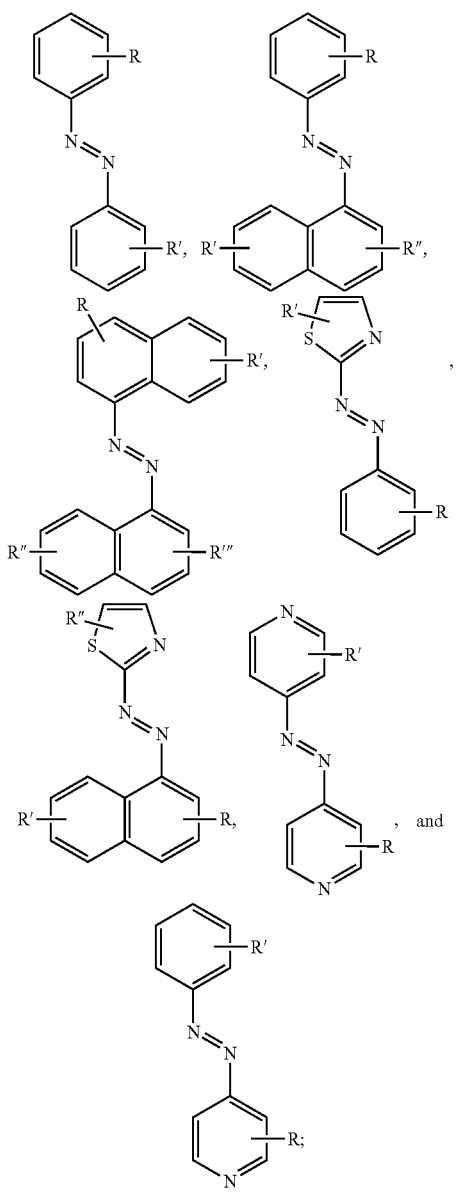

where each SDA-enhancing agent includes at least one R group (one or more of R, R', R", and R'"), and where R, R', R", and R'" comprises a hydrophilic moiety. Any hydrophilic moiety is contemplated. In certain preferred embodiments, the hydrophilic moiety has a negative charge. In other embodiments, the hydrophilic moiety has a positive or neutral charge. In certain embodiments, the hydrophilic moiety is selected from: sulfonate, carboxylate, phosphate, phosphonate groups, $NH_2$, $NR''''_2$, OH, N-sulfonylalkyl, O-sulfoalkyl, salts thereof and combinations thereof. In certain embodiments, a single aromatic group of an SDA-enhancing agent comprises more than one hydrophilic moiety. While not being bound by theory, it appears that the diaromatic-azo moiety functions to increase SNR, enhance photoprotection, or both, while the hydrophilic moiety increases the water solubility of the SDA-enhancing agent.

Representative structures for azo compounds that can serve as the SDA-enhancing agent are shown in FIG. 1. These structures are not meant to be limiting, but merely serve to illustrate certain aspects of examples of SDA-enhancing agents having different structural features, e.g., different aromatic moieties with hydrophilic moieties at different positions. In these structures, the SDA-enhancing moiety is the azo-linked aromatic compound and R, R', R", and R'" represent possible positions for groups containing a hydrophilic moiety. (The dotted box in the second formula from the right in the top row indicates the SDA-enhancing moiety.) As discussed herein, an SDA-enhancing agent has at least one hydrophilic moiety (i.e., at least one hydrophilic moiety in any one of R, R', R", and R'"). In certain embodiments, an SDA enhancing agent includes an additional moiety (i.e., it has at least two R groups) that may contain another hydrophilic moiety or may contain another moiety having a different property or function, e.g., hydrophobic property or binding activity. For example, in certain embodiments, an additional R group (i.e., in addition to the first R group containing a hydrophilic moiety) comprises a non-hydrophilic moiety, e.g., a hydrophobic moiety, a member of a binding pair (e.g., biotin, streptavidin, etc.), or both. Examples of non-hydrophilic moieties include, e.g., amide, $NO_2$, O-alkyl, alkyl, and combinations thereof. In some cases, additional R groups provide additional water solubility, hydrophilicity, and/or adjust the electron density to control or "tune" the absorbance spectrum, e.g., depending on the emission wavelength of fluorophores in the reaction mixture. Any R group may also include additional moieties, e.g., linkers, a member of a binding pair, e.g., biotin, etc., or combinations thereof. In FIG. 1, the formulas second and third from the left on the top row are each a subset of the formula on the far left on the top row, one with the R group positioned at position 4 of the top aromatic ring the other with the R group at position 2 of the top aromatic ring. As noted above, exemplary hydrophilic moieties comprise one or more charged groups, including but not limited to carboxylic acid groups, sulfonic acid groups, phosphate groups, phosphonate groups, and salts thereof.

In certain specific embodiments, an SDA-enhancing agent of the invention is a phenylazobenzoic acid, and a second SNR-enhancing moiety is a salt of phenylazobenzoic acid, e.g., potassium phenylazobenzoate or sodium phenylazobenzoate.

In certain embodiments, any R group listed in FIG. 1 (i.e., any of R, R', R", and R'"), where present, can also comprise a linker that connects the SDA-enhancing moiety to the R group, e.g., an R group comprising a hydrophilic moiety. In certain embodiments, the end of the linker proximal to the SDA-enhancing moiety may comprise a carbonyl, sulfonyl, or phosphonyl group that is bound to the aromatic ring. The linker may comprise charged groups along its length, and in such cases would be considered part of the hydrophilic moiety. Alternatively, the charged moieties of the hydrophilic moiety may be linked at one end of the linker, e.g., the end that is distal from the SDA-enhancing moiety.

In certain embodiments, the SDA-enhancing moiety is characterized by a lipophilicity that can provide for momentary localization of the SDA-enhancing agent near the reaction site, e.g., within or near the observation volume. In some embodiments, the SDA-enhancing agent is localized on a surface of a confined reaction site, e.g., a zero-mode waveguide, nanochannel, nanopore, etc. The localization of the SDA-enhancing agent near the reaction site reduces the background noise from the diffusing labeled reactants (a.k.a., the "diffusion background") as they diffuse within the observation volume. For example, in certain embodiments a relatively lipophilic arylazobenzoic acid or phenylazobenzoic acid, or a salt thereof (e.g., potassium or sodium salt thereof), serves as the SDA-enhancing moiety. Further, the absorption wavelength and the lipophilicity of the SNR-enhancing moiety can be altered by substitutions on the aryl moiety. For example, an addition of a dimethylamino group to the aryl moiety red-shifts the absorption from about 300 nm to 450 nm, and is expected to increase the lipophilicity of the molecule as well.

In certain preferred embodiments, the hydrophilic moiety serves to both repel incoming negatively charged, labeled reactants and increase the water solubility and hydrophilicity of the SDA-enhancing agent. In specific embodiments, the hydrophilic moiety comprises one or more sulfonyl groups, e.g., at least two or three sulfonyl groups. The sulfonyl groups both increase the bulkiness of the labeled nucleoside polyphosphate and its hydrophilicity. Other charged groups that can be included in the hydrophilic moiety include, but are not limited to, phosphate groups, phosphonate groups, carboxylate groups, and the like. Further, different salts of these charged groups can be used, e.g., potassium or sodium salts of the charged groups.

In certain embodiments, a SDA-enhancing agent comprising an SDA-enhancing moiety and a hydrophilic moiety can be linked to another reaction component or to a reaction site to bring the SDA-enhancing agent into close spatial proximity to the volume of the reaction mixture subjected to the illumination. For example, the SDA-enhancing agent may be linked to one or more of a reactant (e.g., a substrate for an enzyme (e.g., a nucleic acid, polypeptide, sugar, or monomers thereof), a fluorescent or fluorogenic label (e.g., a fluorescent dye or quantum dot), an enzyme or other reactive protein or cofactor thereof (e.g., a polymerase, ligase, receptor, antibody, or nuclease)), a reaction site at which the reaction will take place (e.g., within a well, chip, fiber, bead, micro- or nano-channel, nanopore, optical confinement (e.g., zero-mode waveguide (ZMW)), etc.), or a combination thereof (See, e.g., U.S. Patent Publication No. 20090325260, incorporated herein by reference in its entirety for all purposes.) Preferably, the SDA-enhancing agent is not linked directly to a labeled molecule that is intended to be detected during an analytical reaction. In certain embodiments, the invention provides methods and compositions for nucleic acid analysis in which a SDA-enhancing agent is linked to an enzyme or reactive protein that interacts with a substrate or ligand comprising a fluorescent dye. For example, where such enzyme or reactive protein is immobilized at a reaction site by a linker construct, the SDA-enhancing agent can be integrated into the structure of the linker construct in a way that will not interfere with detection of a labeled reactant, or optionally can be linked to the enzyme or reactive protein at a location that is distal from the active site. In other embodiments, the SDA-enhancing agent is free in solution, diffusing throughout the reaction mixture, which simplifies use of the agent since linkage to other reagents, surfaces, linkers, etc. is not required, but it may necessitate a higher concentration of the agent in the reaction mixture.

In certain embodiments, the SDA-enhancing agent is selected from the compounds listed in Table 1 (i.e., any of SDA-enhancing agent nos. 1 to 28 in Table 1).

The invention is generally applicable to any of a variety of optical assays that involve illumination and/or photoactivated conversion or excitation of chemical groups, e.g., fluorophores to detect specific events involving a small number, e.g. one, labeled reactant in a background of many labeled reactants, e.g., free in solution. For example, the compositions and methods provided herein may be used with fluorescence microscopy, optical traps and tweezers, spectrophotometry, fluorescence correlation spectroscopy, confocal microscopy, near-field optical methods, fluorescence resonance energy transfer (FRET), structured illumination microscopy, total internal reflection fluorescence microscopy (TIRF), etc., all of which are well known techniques that are routinely used by those of skill in the art.

Although cyanine dye 3.5 and 5 were used in the Examples described herein, use of the SDA-enhancing agents is not limited to these dyes. Other cyanine dyes are contemplated for use with the SNR-enhancing agents provided herein, e.g., Cy2, Cy3, Cy3B, Cy5.5, and Cy7. Further, other types of dyes well known in the art are also contemplated, including but not limited to coumarin dyes, rhodamine- and fluorescein-based dyes from, e.g., GE Healthcare, and the AlexaFluor® dyes available from Life Technologies, Inc. A wide variety of organic dye structures have been previously described in the art.

One particularly apt example of analyses that benefit from the invention are single-molecule biological analyses, including, inter alia, single-molecule nucleic acid sequencing analyses, single-molecule enzyme analyses, hybridization or binding assays (e.g., antibody assays), nucleic acid hybridization assays, nucleic acid sequencing assays, protein sequencing assays, polymerization assays, ligation reactions, catalytic reactions, detection of reactants within a small volume, e.g., a microfluidic channel or nanopore, and the like, where the reagents of primary import are subjected to illumination and optically observed within a reaction mixture comprising a large number of labeled reagents. In certain embodiments, the methods, compositions, and systems are used in nucleic acid sequencing processes that rely on detection of fluorescent or fluorogenic reagents, e.g., dye-labeled nucleotides or analogs thereof. Examples of such nucleic acid sequencing technologies include, for example, SMRT® nucleic acid sequencing (described in, e.g., U.S. Pat. Nos. 6,399,335, 6,056,661, 7,052,847, 7,033, 764, 7,056,676, 7,361,466, 7,416,844; U.S. Patent Publication No. 20100311061; and in Eid, et al. (2009) Science 323:133-138, the full disclosures of which are incorporated herein by reference in their entireties for all purposes), non-real time, or "one base at a time" sequencing methods available from, e.g., Illumina, Inc. (San Diego, Calif.) and Helicos BioSciences (Cambridge, Mass.), Clonal Single Molecule Array™, nanopore sequencing utilizing optically detectable labels (Genia Technologies (part of Roche Sequencing) and Oxford Nanopore (Oxford, UK)), and SOLiD™ sequencing (Life Technologies). Methods for single-molecule protein sequencing are provided, e.g., in U.S. Patent Publication No. 20100317116, which is incorporated herein by reference in its entirety for all purposes.

In embodiments where the SDA-enhancing agent has both SNR-enhancing and photoprotective activities, no additional SNR and/or photoprotective additives are present in reaction mixtures.

In other embodiments, e.g., where the SDA-enhancing agent has predominantly SNR-enhancing activity, one or more photo-induced damage mitigating agents (e.g., reducing agents, oxidizing agents, triplet-state quenchers, free radical quenchers, oxygen scavengers, and/or a combination thereof) may be included in an illuminated reaction along with the SDA-enhancing agents provided herein. Certain examples of photo-induced damage mitigating agents are provided in U.S. Patent Publication Nos. 2007/0128133, 2007/0161017, 2010/0136592, and 2015/0079603 all of which are incorporated herein by reference in their entireties for all purposes. Further, a reducing and oxidizing system (ROXS) can be effective in minimizing photobleaching and blinking of fluorescent dyes. (*Agnew. Chem. Int. Ed,* 2008, 47, 5465-5469, incorporated herein by reference in its entirety for all purposes.) Such photobleaching and blinking can adversely affect the detectability of an emission from a dye, so the presence of an ROXS can facilitate detection at least by reducing these photochemical phenomena. Typically, an ROXS is a multicomponent system, e.g., comprising a pair of TSQ reagents that includes a reducing agent and an oxidizing agent, which can work in concert to speed the relaxation of a dye from its triplet state to its ground state. Examples of such systems include a mixture of methylviologen and ascorbic acid; a combination of nitrobenzoic acid or salts thereof and mercaptoethylamine, e.g., 2-mercaptoetylamine HCL and sodium 2-, 3- and/or 4-nitrobenzoate; and mixtures of nitrobenzoic acid or salts thereof (e.g., potassium 2-nitrobenzoic acid) and other reducing agents, such as DTT (dithiothreitol) or DMAPA (dimethylaminopropylamine). Adding these reagents to an illuminated reaction can be used to mitigate photo-induced damage to other reactants, e.g., an enzyme, and to improve other reaction metrics, as well. In certain embodiments, single-molecule ROX compounds can be added to an analytical reaction in combination with the SNR-enhancing agents provided herein. Certain preferred single-molecule ROX compounds are described in detail in U.S. Patent Application Publication No. 2015/0079603, which is incorporated herein by reference in its entirety for all purposes.

The SDA-enhancing agents herein can also be used in combination with other strategies for increasing the SNR in analytical data, including but not limited to increasing signal strength by using a brighter fluorophore, isolating the reaction events away from the bulk of the reaction mixture, illuminating only a small volume of the reaction mixture that comprises a reaction site, immobilizing one or more reagents at a reaction site, adjusting a concentration of labeled reactants in the reaction mixture, adding one or more quenching agents, or combination thereof.

II. Improving Signal Detection in Illuminated Analyses

Certain aspects of the invention are generally directed to increasing SNR, increasing photoprotection, or both, during illuminated analyses. The terms "illuminated analysis" and "illuminated reaction" are used interchangeably and generally refer to an analytical reaction that is occurring while being illuminated (e.g., with excitation radiation), so as to evaluate the production, consumption and/or conversion of luminescent (e.g., fluorescent or fluorogenic) reactants and/or products. As used herein, the terms "reactant" and "reagent" are used interchangeably. In certain preferred embodiments, the illuminated reaction is a sequencing reaction and a suboptimal SNR, photoprotection, or both, results, directly or indirectly, from the presence of a large quantity of fluorescently labeled nucleoside polyphosphates in the reaction mixture. In other embodiments, the illuminated reaction is a polypeptide sequencing reaction, a binding assay, or a hybridization assay, and a suboptimal SNR, photoprotection, or both, results from the presence of a large quantity of fluorescently labeled tRNAs or amino acids, binding partners (e.g., antibodies, antigens, ligands, receptors, etc.), or nucleic acids in the reaction mixture, respectively.

In one aspect of the invention, the SDA-enhancing agents described herein are particularly suitable for increasing the SNR, enhancing photoprotection, or both, for reactions in small reaction volume concentrations, wherein some reactants may be present, but at very limited concentrations. As generally referred to herein, such limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized, or otherwise confined within a given area (a reaction site, e.g., within a confinement, e.g., a well, nano- or microchannel, or zero-mode waveguide), so as to provide limited quantity of reagents in that given area, and in certain cases, provide small numbers of molecules of such reagents within that given area, e.g., from 1 to 1000 individual molecules, preferably between 1 and 10 molecules.

In certain aspects of the invention, the SDA-enhancing agents described herein are particularly suitable for increasing the SNR, enhancing photoprotection, or both, for reactions in reactions mixtures having a high concentration of labeled reactants, e.g., at least 50, 100, 150, 200, 250, 300, 350, 400, 450, or 500 nM of a labeled reactant, or of each of a plurality of labeled reactants.

In other aspects of the invention, the SDA-enhancing agents described herein are particularly suitable for increasing the SNR, enhancing photoprotection, or both, for reactions in reactions mixtures having a very small observation volume, e.g., where the total reaction volume is much larger. For example, the observation volume is preferably no more than one nanoliter, picoliter, femtoliter, attoliter, or zeptoliter. In certain preferred embodiments, the observation volume is less than one attoliter and greater than one zeptoliter.

In certain embodiments, the SDA-enhancing agents described herein increase the SNR for an analytical reaction by decreasing the background noise at least 5%, including at least 10%, 15%, 20%, 25%, 30%, 40%, or 50%. In other embodiments, the SNR-enhancing agents described herein increase the SNR for an analytical reaction by increasing the signal at least 5%, including at least 10%, 15%, 20%, 25%, 30%, 40%, or 50%. In preferred embodiments, the SDA-enhancing agents described herein increase the SNR for an analytical reaction by both decreasing the noise and increasing the signal. In certain embodiments, the signal that is increased has a wavelength in the visible spectrum, preferably above 300, 400, 500, 550, 600, or 650 nm. Such embodiments are further described in the Examples herein.

The amount of time an illuminated analysis may be carried out before photo-induced damage so substantially impacts the reactants to render the analysis non-useful (e.g., when the reaction prematurely terminates) is referred to as the "photo-induced damage threshold period." A photo-induced damage threshold period is assay-dependent, and is affected by various factors, including but not limited to characteristics of reactants (e.g., enzymes, substrates, binding partners, etc.) in the assay (e.g., susceptibility to photo-induced damage and the effect of such damage on enzyme activity/processivity), characteristics of the radiation source (e.g., wavelength, intensity), characteristics of the signal-generating molecule (e.g., type of emission, susceptibility to photo-induced damage, propensity to enter triplet state, and the effect of such damage on the brightness/duration of the signal), and similar characteristics of other components of the assay. It can also depend on various components of the assay system, e.g., signal transmission and detection, data collection and analysis procedures, etc. It is well within the abilities of the ordinary practitioner to determine an acceptable photo-induced damage threshold period for a given assay, e.g., by monitoring the signal decay for the assay in the presence of a photodamaging agent and identifying a period for which the signal is a reliable measure for the assay, and such analyses can optionally include time course reactions, titrations, and the like. In certain preferred embodiments of the invention, the photo-induced damage threshold period is that period of illuminated analysis during which such photo-induced damage occurs so as to reduce the rate, processivity, fidelity, product formation, or error frequency of the subject reaction by no more than 10%, 20%, 30%, 40%, 50%, 60%, 70%, 80%, or 90% over the same reaction in the absence of such illumination. This impact on the subject reaction is typically due to direct or indirect damage to one or more reaction components, and of particular interest are those present in limiting quantities, e.g., at a low concentration. For example, certain single molecule reactions comprise immobilized reactants that are present as a single molecule at a given reaction site. While other reactants in solution can diffuse in and out of the reaction site, such immobilized reactants are not "exchangeable" in the reaction mixture. As such, damage to these immobilized reactants is typically detrimental to the subject reaction at a given reaction site, and can even cause premature termination of the single reaction being monitored at a reaction site.

In certain embodiments, the invention provides SDA-enhancing agents that, when present, increase the photo-induced damage threshold period in an illuminated reaction, thereby increasing the amount of time reactions can proceed toward completion with minimal damage to the reactants, thereby lengthening the time in which a detectable signal is an accurate measure of reaction progression. In particular, it is an object to reduce damage to reactants at limiting concentrations, e.g., immobilized reactants, and especially those present as single molecules at a reaction site.

In some contexts, a reaction comprising one or more components that have been subject to photo-induced damage may be subject to spurious activity, and thus be more active than desired. In such cases, it will be appreciated that the photo-induced damage threshold period of interest would be characterized by that period of illuminated analysis during which such spurious activity, e.g., as measured by an increase in reaction rate, or an increase in non-specific reaction rate, is no more than 10% over a non-illuminated reaction, no more than 20% over a non-illuminated reaction, no more than 50% over a non-illuminated reaction, and in some cases, no more than 90% over a non-illuminated reaction. In one non-limiting example, where a nucleic acid polymerase, by virtue of a photodamaging event, begins to incorrectly incorporate nucleotides (or analogs or derivatives thereof) during template directed synthesis, such activity would impact the photo-induced damage threshold period as set forth above. In this case, the SDA-enhancing agents and methods of the invention would increase the photo-induced damage threshold period, thus increasing the amount of time the reaction could be illuminated before the above-described spurious activity occurred.

With reference to nucleic acid analyses, it has been observed that in template-directed synthesis of nucleic acids using fluorescent nucleotide analogs as a substrate, prolonged illumination can result in a substantial degradation in the ability of the polymerase to synthesize the nascent strand of DNA, as described previously, e.g., in U.S. Published Patent Application No. 2007/0161017, incorporated by reference herein in its entirety for all purposes. Damage to polymerase enzymes, template sequences, and/or primer sequences can significantly hinder the ability of the polymerase to process longer strands of nucleic acids. For example, reduction in the processivity of a polymerase leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. Such a reduction in the activity of an enzyme can have significant effects on many different kinds of reactions in addition to sequencing reactions, such as ligations, cleavages, digestions, phosphorylations, other types of polymerizations, etc.

The photo-induced damage sought to be prevented by the methods and compositions of the invention is not merely photo-induced damage to fluorescent reagents, e.g., photobleaching, but is also directed to prevention or reduction of the downstream effects of photoactivation of such fluorescent reagents, e.g., during interaction with or proximity to other reagents, and in particular those that are of limited quantity in a reaction mixture, and as such, their limited presence is more greatly impacted by even slight losses due to photo-induced damage. For example, and without being bound to a theory of operation, photo-induced damage to reactive proteins, enzymes, or other reactants may include damage to the reactants or irreversible interactions between such reactants and the photo-induced damaged reagents. Such interactions may be covalent or noncovalent interactions, binding interactions, transient interactions, catalytic interactions, and the like. As suggested by the foregoing, photo-induced damage generally refers to an alteration in a given reagent, reactant, or the like, that causes such reagent to have altered functionality in a desired reaction, e.g., reduced activity, reduced specificity, or a reduced ability to be acted upon, converted, or modified, by another molecule, that results from, either directly or indirectly, a photo-induced reaction, e.g., a photo-induced reaction creates a reactant that interacts with and causes damage to one or more other reactants. Typically, such a photoreaction directly impacts either the reactant of interest, e.g., direct photo-induced damage, or impacts a reactant within one, two or three reactive steps of such reactant of interest. Further, such photoreaction can directly impact the reaction of interest, e.g., causing a change in rate, duration, processivity, product formation, or fidelity of the reaction.

In general, the SDA-enhancing agents described herein are present in the reaction mixture at levels sufficient to provide beneficial impact, e.g., increase SNR (reducing noise and/or increasing optical signal) and/or to provide enhanced photoprotection, but are not present at levels that interfere substantially with the reaction of interest, e.g., the sequencing reaction. In certain preferred embodiments, the SDA-enhancing agent is provided in a reaction mixture at a concentration of, e.g., 10 mM or lower, 8 mM or lower, 6 mM or lower, 4 mM or lower, 2 mM or lower, 1 mM or lower, 900 µM or lower, 500 µM or lower, 200 µM or lower, or 100 µM or lower. In some preferred embodiments, the SNR-enhancing agent is provided in a reaction mixture at a concentration of about 300 µM to 1 mM, e.g., 300 µM, 400 µM, 500 µM, 600 µM, 700 µM, 800 µM, 900 µM, or 1 mM. However, these concentrations are merely exemplary and may be change depending on various factors including, e.g., the particular fluorescent or fluorogenic labels present in a reaction, the type of reaction to which it is added, conditions under which such reaction is to be performed, and the like. Such adjustments are well within the abilities of the ordinary practitioner.

An SDA-enhancing agent present in illuminated reactions comprises an SDA-enhancing moiety and a hydrophilic moiety (as described above). In brief, in certain embodiments, an SDA-enhancing moiety of an SDA-enhancing agent comprises where the SDA-enhancing moiety comprises an azo group of the formula $R_a$—N=N—$R_b$, where both $R_a$ and $R_b$ comprise an aromatic moiety, and where $R_a$ comprises a hydrophilic moiety. The N=N group is referred to as an azo group. In certain embodiments, both $R_a$ and $R_b$ comprise a hydrophilic moiety (either the same hydrophilic moiety or different hydrophilic moieties). In certain embodiments, the aromatic moieties of $R_a$ and $R_b$ are the same while in other embodiments, the aromatic moieties are different. In certain embodiments, the aromatic moiety of $R_a$ and $R_b$ are selected from: aryl compounds, heterocyclic aromatic compounds, polycyclic aromatic compounds, and combinations thereof. In certain embodiments, the SDA-enhancing agent comprises an azo-diaryl compound. In certain embodiments, the SDA-enhancing agent has formula selected from:

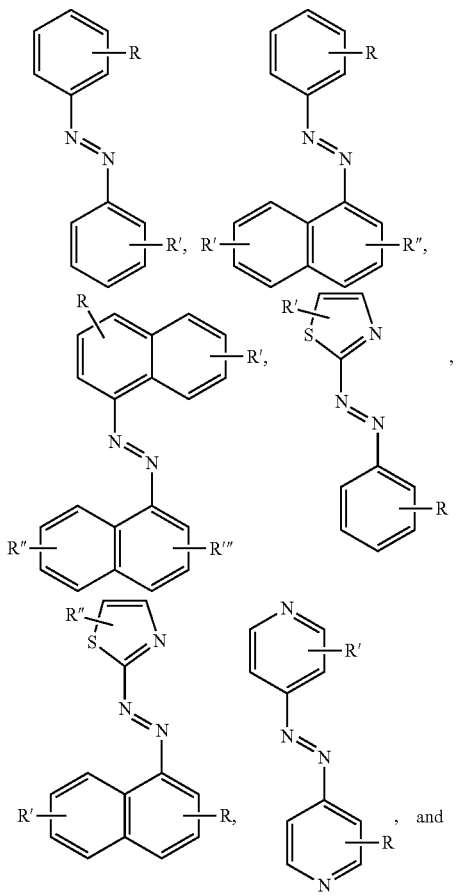

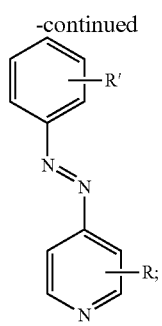

where each SDA-enhancing agent includes at least one R group (one or more of R, R', R", and R'"), and where R, R', R", and R'" comprises a hydrophilic moiety. Any hydrophilic moiety is contemplated. In certain preferred embodiments, the hydrophilic moiety has a negative charge. In other embodiments, the hydrophilic moiety has a positive or neutral charge. In certain embodiments, the hydrophilic moiety is selected from: sulfonate, carboxylate, phosphate, phosphonate groups, $NH_2$, $NR""_2$, OH, N-sulfonylalkyl, O-sulfoalkyl, salts thereof and combinations thereof. In certain embodiments, a single aromatic group of an SDA-enhancing agent comprises more than one hydrophilic moiety. While not being bound by theory, it appears that the diaromatic-azo moiety functions to increase SNR, enhance photoprotection, or both, while the hydrophilic moiety increases the water solubility of the SDA-enhancing agent.

SNR-enhancing agents of the invention include, but are not limited to a compound of a formula selected from the group of compounds listed in Table 1 (i.e., SDA-enhancing agent nos. 1 to 28).

Optionally, the methods further comprise confining at least one component of the reaction mixture on a substrate, e.g., a substrate that includes one or more zero-mode waveguides.

Measurements of increase in SNR or photoprotection as a result of inclusion or treatment with one or more SDA-enhancing agents may be characterized in any manner suitable for the assay being performed.

For example, increased SNR can be characterized as providing at least one of an increase in brightness of a signal over that detected in an untreated reaction, and a decrease in background noise that brings the noise below that detected in an untreated reaction. SDA-enhancing agents are preferably characterized as both increasing signal and decreasing background. Further, characterization of an increase in SNR generally utilizes measurements of signal brightness and baseline noise over the course of a reaction, and comparing the ratio of signal to noise observed in a reaction comprising an SDA-enhancing agent to the ratio observed in a control reaction mixture lacking the SDA-enhancing agent. These analyses generally involve well established laboratory methods, such as time course reactions, titrations, and the like.

In the case of the present invention, the inclusion of an SDA-enhancing agent(s) of the invention that increase SNR generally results in a greater than 5%, 10%, 15%, 20%, 25%, 30%, 40% or 50% increase in SNR as compared to a reaction lacking the SDA-enhancing agent. In the case of the present invention, the inclusion of SDA-enhancing agent(s) of the invention that increase SNR generally results in a greater than 5%, 10%, 15%, 20%, 25%, or 30% increase in brightness as compared to a reaction lacking the SDA-enhancing agent. In the case of the present invention, the inclusion of SDA-enhancing agent(s) of the invention that increase SNR generally results in a greater than 5%, 10%, 15%, 20%, or 25% decrease in background noise as compared to a reaction lacking the SDA-enhancing agent.

Measurements of reduction of photo-induced damage as a result of inclusion or treatment with one or more SDA-enhancing agents having photoprotective activity may be characterized as providing a reduction in the level of photo-induced damage over a control reaction lacking the SDA-enhancing agent. Further, characterization of a reduction in photo-induced damage generally utilizes a measurement of reaction rates, durations, processivities, product formation, or fidelities, e.g., of enzyme activity, and/or a comparison of the photo-induced damage threshold period, between a treated reaction mixture and an untreated reaction mixture. These analyses generally involve well established laboratory methods, such as time course reactions, titrations, and the like.

In the case of the present invention, the inclusion of SDA-enhancing agents of the invention having photoprotective activity generally results in a reduction of photo-induced damage of one or more reactants in a given reaction, as measured in terms of "prevented loss of reactivity" in the system. Using methods known in the art, the amount of prevented loss of activity can be at least 10%, preferably greater than 20%, 30%, or 40%, and more preferably at least 50% reduction in loss of reactivity, and in many cases greater than a 90% and up to and greater than 99% reduction in loss of reactivity. By way of illustration, and purely for the purpose of example, when referring to reduction in photo-induced damage as a measure of enzyme activity in the presence and absence of an SDA-enhancing agent of the invention having photoprotective activity, if a reaction included a reaction mixture having 100 units of enzyme activity that would, in the absence of the SDA-enhancing agent and following illuminated analysis, yield a reaction mixture having only 50 units of activity, then a 10% reduction in photo-induced damage would yield a final reaction mixture of 55 units (e.g., 10% of the 50 units otherwise lost, would no longer be lost). Similarly, "prevented loss of reactivity" can be computed in terms of reaction rates, product formation, processivity, fidelity, and other metrics of a given analytical reaction. Photoprotective activity of an SDA-enhancing agent also can increase the brightness and/or improve the detection characteristics of an optical signal in an illuminated reaction (as described above).

The improvements in signal detection provided by inclusion of SDA-enhancing agents of the present invention can be exploited to enhance a number of different signal detection assays. For example, the increased SNR and/or enhanced photoprotective effects of SDA-enhancing agents can lead directly to increases in the accuracy of sequencing reactions, e.g., single molecule sequencing reactions, e.g., as implemented on SMTR® Sequencing platforms from Pacific Biosciences (Menlo Park Calif.). Accuracy can be improved by up to 15% over control sequencing reactions that lack the SDA-enhancing agent, e.g., 1%, 2%, 3%, 4%, 5%, 7%, 10%, 12%, 15% and anywhere in between.

In accordance with the present invention, SDA-enhancing agents may generally be provided as a component of the reaction mixture, either through addition as an additive, either liquid or solid, and can be predisposed and/or immobilized within the region where the reaction is taking place, or may be provided in a configuration that permits them to freely interact with the aqueous system components by including such agents within or linked to structures (e.g., caging groups, tridentate structures, etc.) that render the agents suspended in aqueous systems and additionally available to interact with relevant portions of the reaction mixture, e.g., labeled reactants. By way of example, in cases where the reaction of interest is confined to a particular region or location, it may be desirable to immobilize or otherwise localize the SDA-enhancing agents within or proximal to that region, e.g., upon the surfaces of the substrates or reactions wells.

As used herein, a substrate may comprise any of a variety of formats, from planar substrates, e.g., glass slides or planar surfaces within a larger structure, e.g., a multi-well plates such as 96-well, 384-well, and 1536-well plates, or regularly spaced micro- or nano-porous substrates (e.g., arrays of zero-mode waveguides). Such substrates may also comprise more irregular porous materials, such as membranes, aerogels, fibrous mats, or the like, or they may comprise particulate substrates, e.g., beads, spheres, metal or semiconductor nanoparticles, optical fibers, or the like.

In certain embodiments, the compounds provided herein may be used in combination with one another and/or with a variety of reducing agents, anti-fade agents, free radical quenchers/scavengers, oxygen scavengers, singlet oxygen quenchers, photoprotective compounds, and/or triplet-state quenchers (e.g., 6-hydroxy-2,5,7,8-tetramethylchroman-2-carboxylic acid), including, for example, those provided in U.S. Patent Publication Nos. 2007/0161017 and 2010/0136592, incorporated herein by reference, which provide methods of mitigating the impact of photo-induced damage on the results of a given analytical operation that may be used with the compounds and methods of the provided herein. Addition of these compounds is particularly useful in the optical interrogation of reactions where components of the reaction that are susceptible to photo-induced damage are spatially confined on an assay plate or substrate, either through the presence of structural confinements, optical confinements, and/or through immobilization of the components. Examples of such confined reagents include surface immobilized or localized reagents, e.g., surface immobilized or associated enzymes, receptors, antibodies, etc. that are interrogated upon the surface, e.g., through fluorescence scanning microscopy or scanning confocal microscopy, total internal reflectance microscopy or fluorometry, surface imaging, or the like.

In addition to the foregoing, it will be appreciated that the other reagents in a given reaction of interest may be provided in any of a variety of different configurations. For example, they may be provided free in solution, or complexed with other materials, e.g., other reagents and/or solid supports. Likewise, such reagents may be provided coupled to beads, particles, nanocrystals or other nanoparticles, or they may be tethered to larger solid supports, such as matrices or planar surfaces. These reagents may be further coupled or complexed together with other reagents, or as separate reagent populations or even as individual molecules, e.g., that are detectably resolvable from other molecules within the reaction space. Whether a particular reagent is confined by virtue of structural barriers to its free movement or is chemically tethered or immobilized to a surface of a substrate, it will be understood as being confined. For example, in some preferred embodiments, one or more reagents in an assay system are confined within a spatial confinement, which may be an internal reflection confinement (IRC) or an external reflection confinement (ERC), a zero-mode waveguide, a nanopore, a microchannel or nanochannel, or an alternative structure, such as one comprising porous film with reflective index media or a confinement using index matching solids. More detailed descriptions of various types of confinements are provided, e.g., in International Application Publication No. WO/2006/083751, U.S. Pat. No. 6,917,726, and U.S. Pat. No. 7,170,050, the full disclosures of which are incorporated herein by reference in their entireties for all purposes.

III. Exemplary Applications

As noted above, the methods and compositions of the invention are useful in a broad range of illuminated analytical reactions, and particularly those using photoluminescent or fluorescent reactants, and particularly such reactions where the labeled reagents are at a high enough concentration to produce sufficient background noise to interfere with detection of an informational signal during the reaction. One exemplary application of the methods and compositions described herein is in single molecule analytical reactions, where the reaction of a single molecule (or very limited number of molecules) is observed in the analysis, such as observation of the action of a single enzyme, receptor, or antibody molecule. The SDA-enhancing agents provided herein have been shown to (i) increase SNR by both decreasing background noise and increasing signal, which improves detection of the signal and/or (ii) provide photoprotective activity. In doing so, the SDA-enhancing agents of the present invention increases the accuracy and/or amount of the data being collected.

In an exemplary embodiment, the SDA-enhancing agents provided herein are used in illuminated reactions for single-molecule analysis, including sequencing of nucleic acids by observing incorporation of nucleotides or nucleotide analogs into a nascent nucleic acid sequence during template-directed polymerase-based synthesis. Such methods, generally referred to as "sequencing-by-incorporation," often involve the observation of the addition of nucleotides or nucleotide analogs in a template-dependent fashion in order to determine the sequence of the template strand. See, e.g., U.S. Pat. Nos. 6,780,591, 7,037,687, 7,344,865, 7,302,146; U.S. Patent Publication Nos. 20100075327 and 20070036511; U.S. patent application Ser. No. 12/767,673, filed Apr. 26, 2010; U.S. patent application Ser. No. 12/635,618, filed Dec. 10, 2009; and Eid, et al. (2009) Science 323:133-138, all of which are incorporated herein by reference in their entireties for all purposes. Processes for performing this detection typically include the use of fluorescently labeled nucleotide analogs within a confined observation region, e.g., within a nanoscale well and/or tethered, either directly or indirectly to a surface. By using excitation illumination (i.e., illumination of an appropriate wavelength to excite the fluorescent label and induce a detectable signal), the fluorescently labeled bases can be detected as they are incorporated into the nascent strand, thus identifying the nature of the incorporated base, and as a result, the complementary base in the template strand. It will be understood that many different kinds of reactions can also benefit through use of the methods, compositions, and systems provided herein, e.g., including those described in U.S. patent application Ser. Nos. 12/813,968 and 12/814,075, both of which were filed Jun. 11, 2010, and are incorporated herein by reference in their entireties for all purposes.

One particularly preferred aspect of the invention is in conjunction with the sequencing by incorporation of nucleic acids within a structural or optical confinement, such as a micro- or nano-channel, a nanopore, or a zero-mode waveguide. Such reactions involve observation of an extremely small reaction volume in which one or only a few polymerase enzymes and their fluorescent substrates may be present. Zero-mode waveguides, and their use in sequencing applications are generally described in U.S. Pat. Nos. 6,917,726 and 7,033,764, and preferred methods of sequencing by incorporation are generally described in Published U.S. Patent Application No. 2003/0044781, the full disclosures of which are incorporated herein by reference in their entireties for all purposes, and in particular, for their teachings regarding such sequencing applications and methods. Briefly, arrays of zero-mode waveguides ("ZMWs"), configured in accordance with the present invention may be employed as optical confinements for single molecule analytical reactions, e.g., for nucleic acid (e.g., DNA, RNA) sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, which is immobilized at the base of the ZMW, may then be specifically observed during synthesis to monitor incorporation of nucleotides or nucleotide analogs in a template-dependent fashion, and thus provide the identity and sequences of nucleotides or nucleotide analogs in the template strand. This identification is typically accomplished by providing detectable label groups, such as fluorescent labeling molecules, on the nucleotides or nucleotide analogs. In SMRT® sequencing (Pacific Biosciences), the nucleoside polyphosphates in the reaction mixture are connected to a fluorescent dye by a linker bound to the polyphosphate tail. As such, when the base is incorporated into a nascent nucleic acid strand, the label is released along with the polyphosphate (not including the alpha phosphate) and linker.

In accordance with the present invention, the above-described sequencing reactions may be carried out in the presence of one or more SDA-enhancing agents provided herein, either alone or in combination with other reaction mixture additives, such as reducing agents, antifade agents, free radical quenchers, triplet-state quenchers, singlet oxygen quenchers, or enzyme systems for depletion of oxygen species (e.g., comprising an oxidase).

It is to be understood that the above description is intended to be illustrative and not restrictive. It readily should be apparent to one skilled in the art that various embodiments and modifications may be made to the invention disclosed in this application without departing from the scope and spirit of the invention. For example, in certain embodiments various photo-induced damage mitigating agents and systems can be combined within a single reaction mixture, in particular where their modes of action differ and/or complement one another. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

IV. Embodiments

Aspects of the present disclosure include the following non-limiting embodiments.

1. A method for improving a signal detection assay, the method comprising: providing a reaction mixture comprising a fluorescent or fluorogenic reactant and an unlabeled reactant; adding a signal detection assay (SDA)-enhancing agent to the reaction mixture, wherein the SDA-enhancing agent comprises an SDA-enhancing moiety and a hydrophilic moiety, wherein the SDA-enhancing moiety comprises an azo group of the formula: $R_a$—N═N—$R_b$, wherein both $R_a$ and $R_b$ comprise an aromatic moiety, and wherein the hydrophilic moiety is covalently attached to $R_a$; illuminating the reaction mixture with an excitation illumination; and detecting an emission signal from the illuminated reaction, wherein the SDA-enhancing agent results in an increased signal-to-noise ratio (SNR), enhanced photoprotection, or both, as compared to the illuminated reaction mixture in the absence of the SDA-enhancing agent.

2. The method of embodiment 1, wherein the unlabeled reactant is immobilized at a reaction site.

3. The method of embodiment 2, wherein said reaction site is within a zero-mode waveguide.

4. The method of any one of embodiments 1 to 3, further comprising the step of monitoring a reaction between the fluorescent or fluorogenic reactant and an unlabeled reactant while illuminating the reaction mixture.

5. The method of any one of embodiments 1 to 4, wherein said illuminated reaction is a base extension reaction.

6. The method of any one of embodiments 1 to 5, wherein the unlabeled reactant is an enzyme.

7. The method of embodiment 6, wherein the enzyme is a polymerase, helicase, exonuclease, ribosome, or a ligase.

8. The method of any one of embodiments 1 to 7, wherein the reaction mixture further comprises a template nucleic acid molecule.

9. The method of any one of embodiments 1 to 8, wherein the fluorescent or fluorogenic substrate comprises a nucleoside polyphosphate or analog thereof.

10. The method of any one of embodiments 1 to 9, wherein the aromatic moieties of $R_a$ and $R_b$ are the same.

11. The method of any one of embodiments 1 to 9, wherein the aromatic moieties of $R_a$ and $R_b$ are different.

12. The method of any one of embodiments 1 to 11, wherein the aromatic moiety of $R_a$ and $R_b$ are selected from: aryl compounds, heterocyclic aromatic compounds, polycyclic aromatic compounds, and combinations thereof.

13. The method of any one of embodiments 1 to 12, wherein SDA-enhancing agent comprises: an azo-diaryl compound.

14. The method of any one of embodiments 1 to 13, wherein the SDA-enhancing agent has a formula selected from the group consisting of:

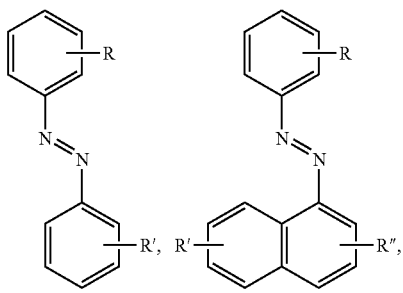

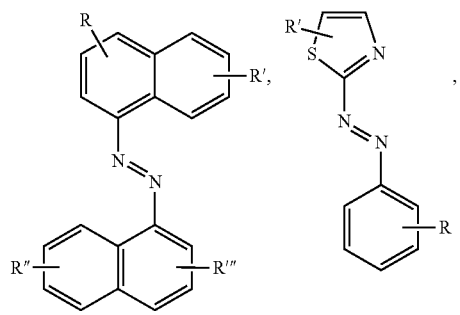

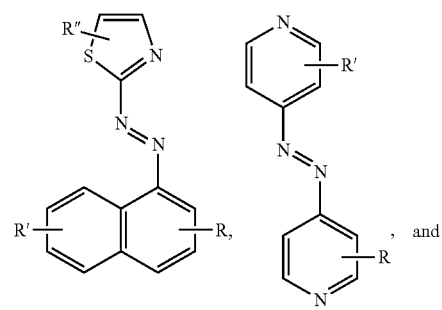

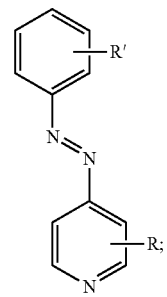

wherein each formula includes at least one R group comprising the hydrophilic moiety.

15. The method of any one of embodiments 1 to 14, wherein the hydrophilic moiety comprises: a sulfonyl group, a sulfonate, a carboxylate, phosphate, a phosphonate group, $NH_2$, $NR''''_2$, OH, N-sulfonylalkyl, O-sulfoalkyl, salts thereof, and any combination thereof.

16. The method of embodiment 15, wherein the hydrophilic moiety comprises a least one sulfonyl group.

17. The method of any one of embodiments 1 to 16, wherein the SNR-enhancing moiety further comprises a linker that links the SNR-enhancing moiety to the hydrophilic moiety.

18. The method of embodiment 17, wherein the linker comprises an alkyl chain of at least two carbons.

19. The method of embodiment 17, wherein the linker comprises a polyethylene glycol chain.

20. The method of any one of embodiments 1 to 19, wherein the SNR-enhancing agent is selected from the group consisting of:

41 42
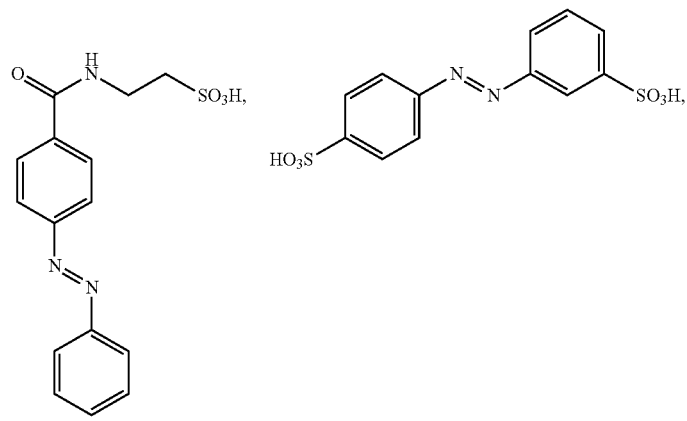
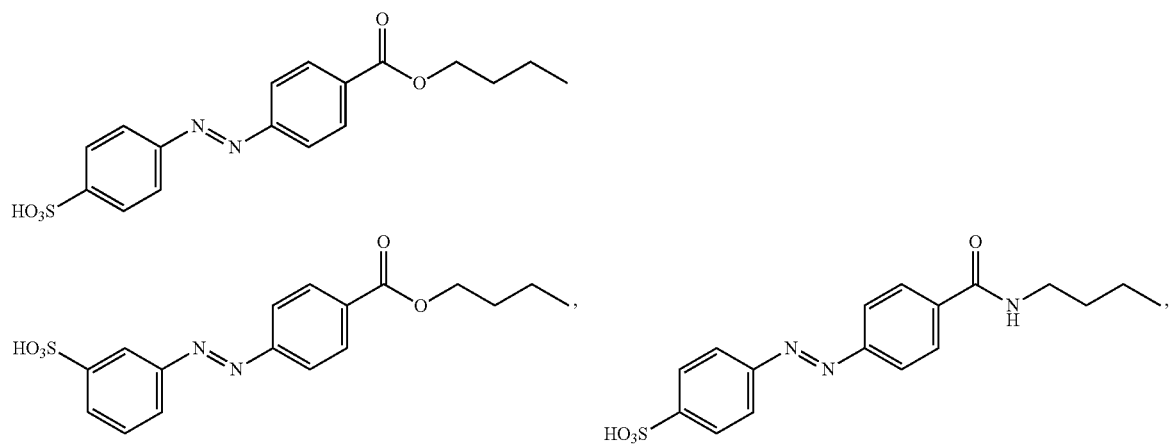
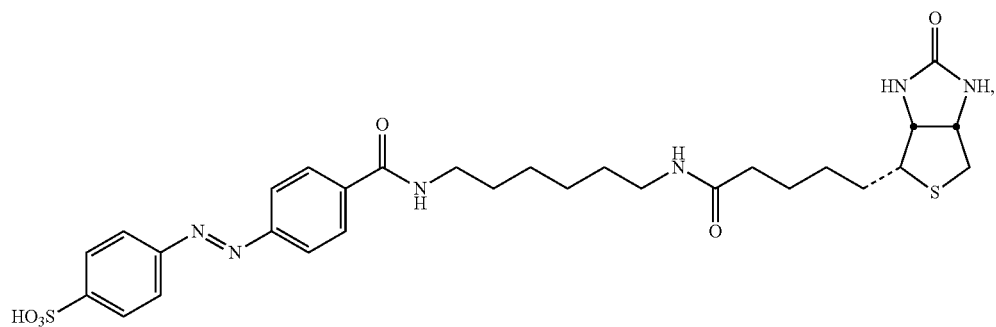
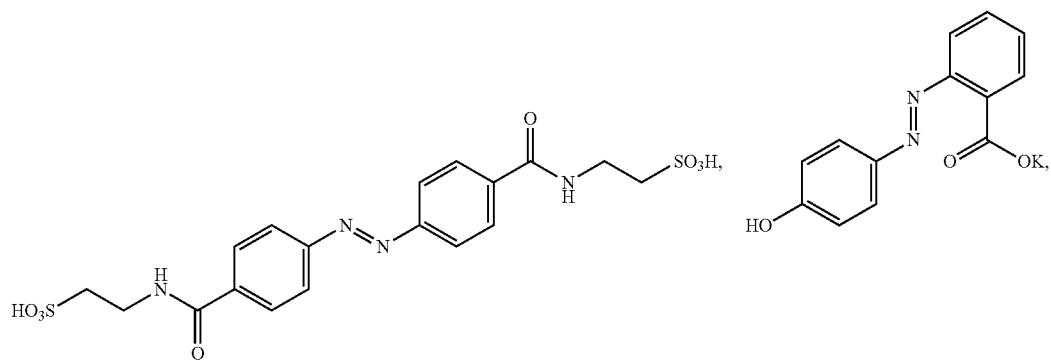

-continued
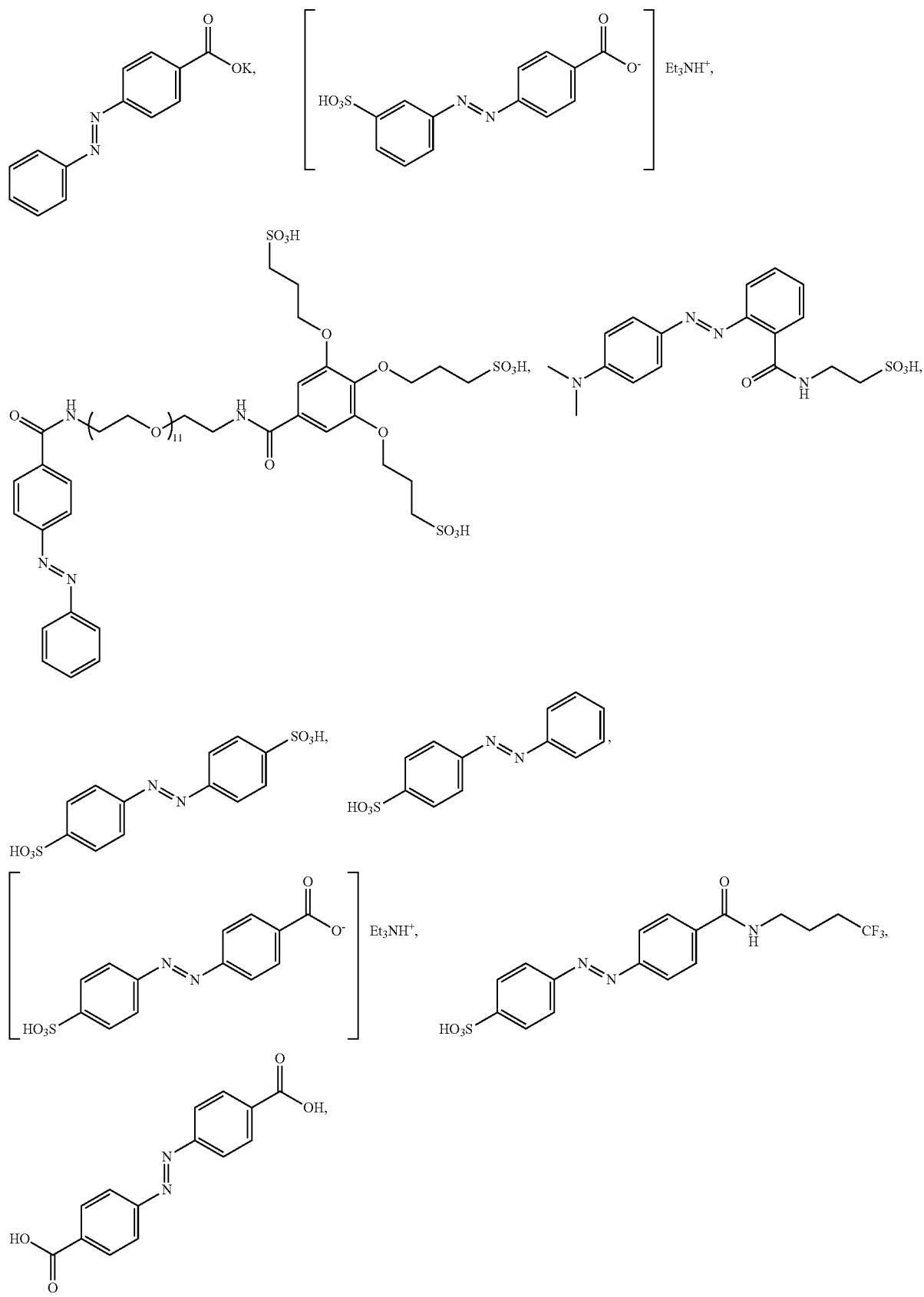

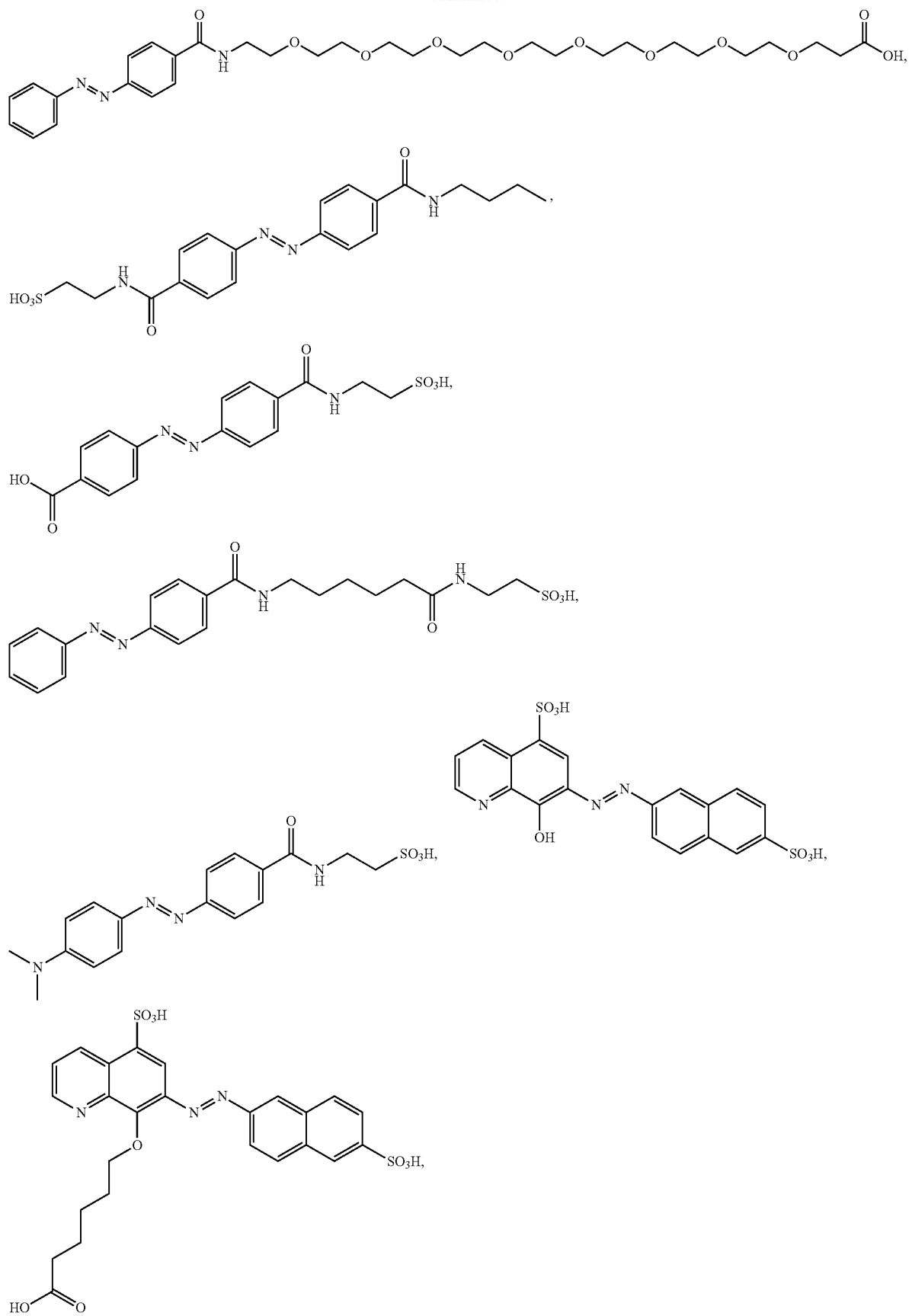

-continued

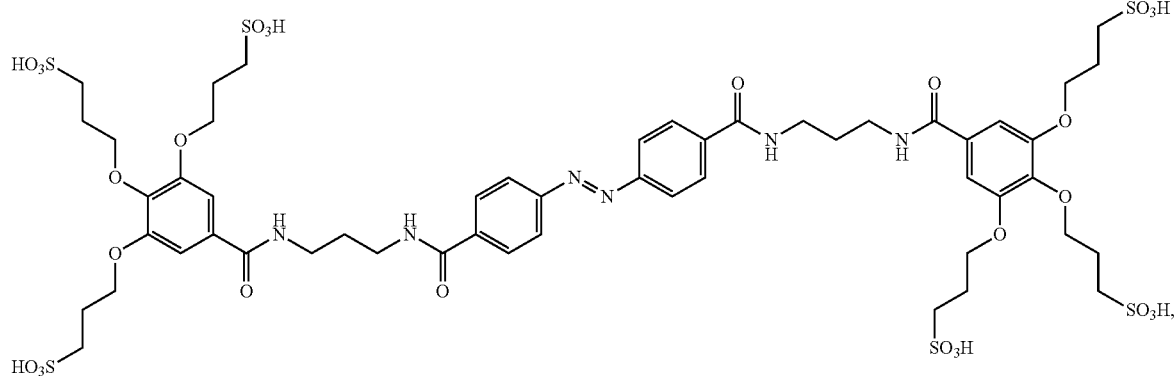

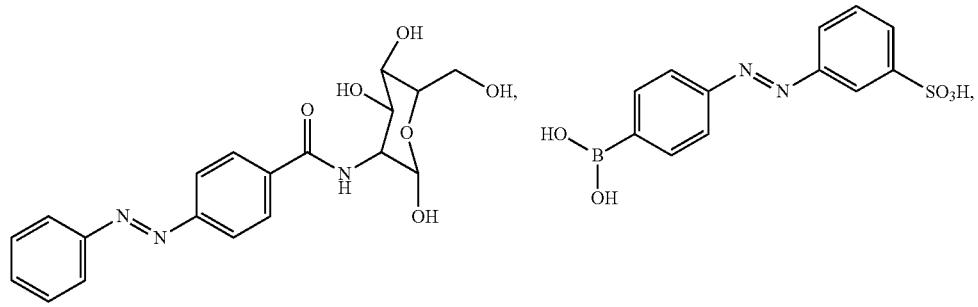

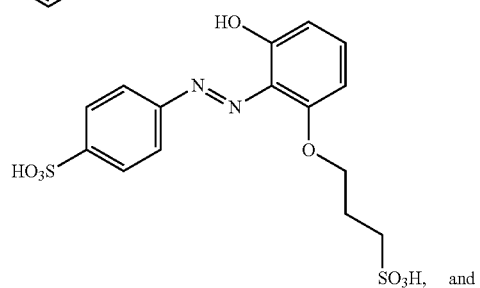

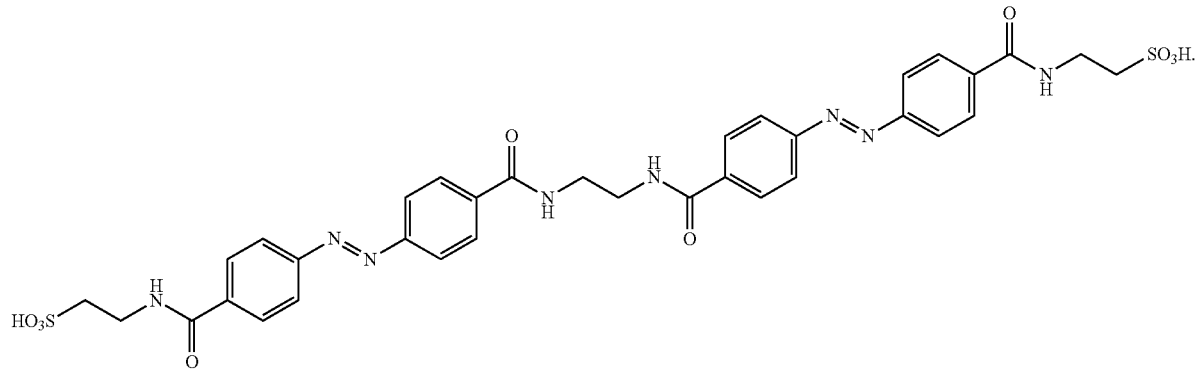

21. The method of any one of embodiments 1 to 20, wherein the SDA-enhancing agent results in any one or any combination of: (i) an increased optical signal, (ii) a reduction in background noise, (iii) mitigation of photoinduced damage (PID) to the unlabeled reactant, and (iv) a reduction in blinking or photobleaching of the fluorescent or fluorogenic reactant, wherein (i) to (iv) are as compared to the illuminated reaction mixture in the absence of the SDA-enhancing agent.

22. The method of any one of embodiments 1 to 21, wherein the SDA-enhancing agent results in both increased SNR and enhanced photoprotection as compared to the illuminated reaction mixture in the absence of the SDA-enhancing agent.

23. The method of any one of embodiments 1 to 22, wherein the signal detection assay is an illuminated sequencing reaction, wherein the accuracy of the sequencing reaction is increased as compared to the illuminated sequencing reaction in the absence of the SDA-enhancing agent.

24. The method of embodiment 23, wherein the reaction mixture comprises: a polymerase, a template nucleic acid, and a fluorescent or fluorogenic nucleotide or nucleotide analog.

25. The method of embodiment 24, further comprising the step of monitoring a reaction between the polymerase and the fluorescent or fluorogenic nucleotide or nucleotide analog while illuminating the reaction mixture.

26. The method of any one of embodiments 24 or 25, wherein said illuminated sequencing reaction is a base extension reaction.

27. The method of any one of embodiments 24 to 26, wherein the polymerase is confined within a zero-mode waveguide.

28. A reaction mixture comprising: a fluorescent or fluorogenic reactant; an unlabeled reactant; and a signal detection assay (SDA)-enhancing agent comprising an SDA-enhancing moiety and a hydrophilic moiety, wherein the SDA-enhancing moiety comprises an azo group of the formula: $R_a$—N=N—$R_b$, wherein both $R_a$ and $R_b$ comprise an aromatic moiety, and wherein the hydrophilic moiety is covalently attached to $R_a$.

29. The reaction mixture of embodiment 28, wherein the fluorescent of fluorogenic reactant comprises one or more labeled nucleotide polyphosphates, the unlabeled reactant comprises a polymerase, and the SDA-enhancing agent is selected from Table 1.

30. A kit comprising: a fluorescent or fluorogenic reactant; an unlabeled reactant; and a signal detection assay (SDA)-enhancing agent comprising an SDA-enhancing moiety and a hydrophilic moiety, wherein the SDA-enhancing moiety comprises an azo group of the formula: $R_a$—N=N—$R_b$, wherein both $R_a$ and $R_b$ comprise an aromatic moiety, and wherein the hydrophilic moiety is covalently attached to $R_a$.

31. The kit of embodiment 30, wherein the fluorescent of fluorogenic reactant comprises one or more labeled nucleotide polyphosphates, the unlabeled reactant comprises a polymerase, and the SDA-enhancing agent is selected from Table 1.

V. Examples

Sequencing Performance in the Presence of SDA-Enhancing Agents

Experiments were conducted using a PacBio® Sequel™ sequencing instrument (Pacific Biosciences, Menlo Park, Calif.) according to manufacturer's instructions for 10-minute movies. A small template nucleic acid (~300 bp SMRT-bell™ template) was sequenced using SMRT® Sequencing, which is a single-molecule, real-time sequencing method wherein a sequencing read is generated by performing a sequencing-by-synthesis reaction on single template molecule and observing base incorporation. The nucleotides in the reaction have a fluorescent label linked to the phosphate tail such that upon incorporation of the base, the label is released with the polyphosphate. The labels on the nucleotides in the reaction are as follows: Cyanine 3.5-labeled deoxythymidine (Cy3.5-dT); Cyanine 5-labeled deoxyadenosine (Cy5-dA); Cyanine 3.5-labeled deoxyguanosine (Cy3.5-dG); and Cyanine 5-labeled deoxycytidine (Cy5-dC). The level of fluorescence emitted from the nucleotides labeled with the same label are quantitatively different, and thus can be distinguished from each other in the reaction. Thus, the level of fluorescence emitted from Cy3.5-dT and Cy3.5-dG during the illumination reaction is different enough to distinguish between them in the sequencing reaction and the same is true for Cy5-dA and Cy5-dC. It is noted that different labels (i.e., other than Cyanine 3.5 and Cyanine 5) and/or different labeling configurations can be employed. This assay configuration is thus not meant to be limiting. vary, and include cyanine dyes 3.5 and 5. The fluorescent characteristic for each dye (wavelength, intensity, etc.) is unique to one specific deoxynucleotide and thus can be analyzed to positively identify when it is incorporated into a growing nucleic acid strand. Although only a very small volume of the reaction mixture is illuminated, the relatively high concentration of nucleotides required for polymerase activity results in background noise that can interfere with the detection of an incorporation event. Addition of an SDA-enhancing agent was found to enhance SNR and the accuracy of the sequencing reaction. Unexpectedly, this accuracy increase was maintained even in the absence of a known triplet state quencher which we had previously shown to be needed for providing photostability to the reaction components (see below). Thus, the SDA-enhancing agent not only increased SNR but also provided an unexpected photoprotective function for these reactions. This dual activity resulted in better detection of incorporation and more accurate sequence reads even in the absence of a separate photoprotective agent (e.g., a triplet state quencher).

Figure 2:
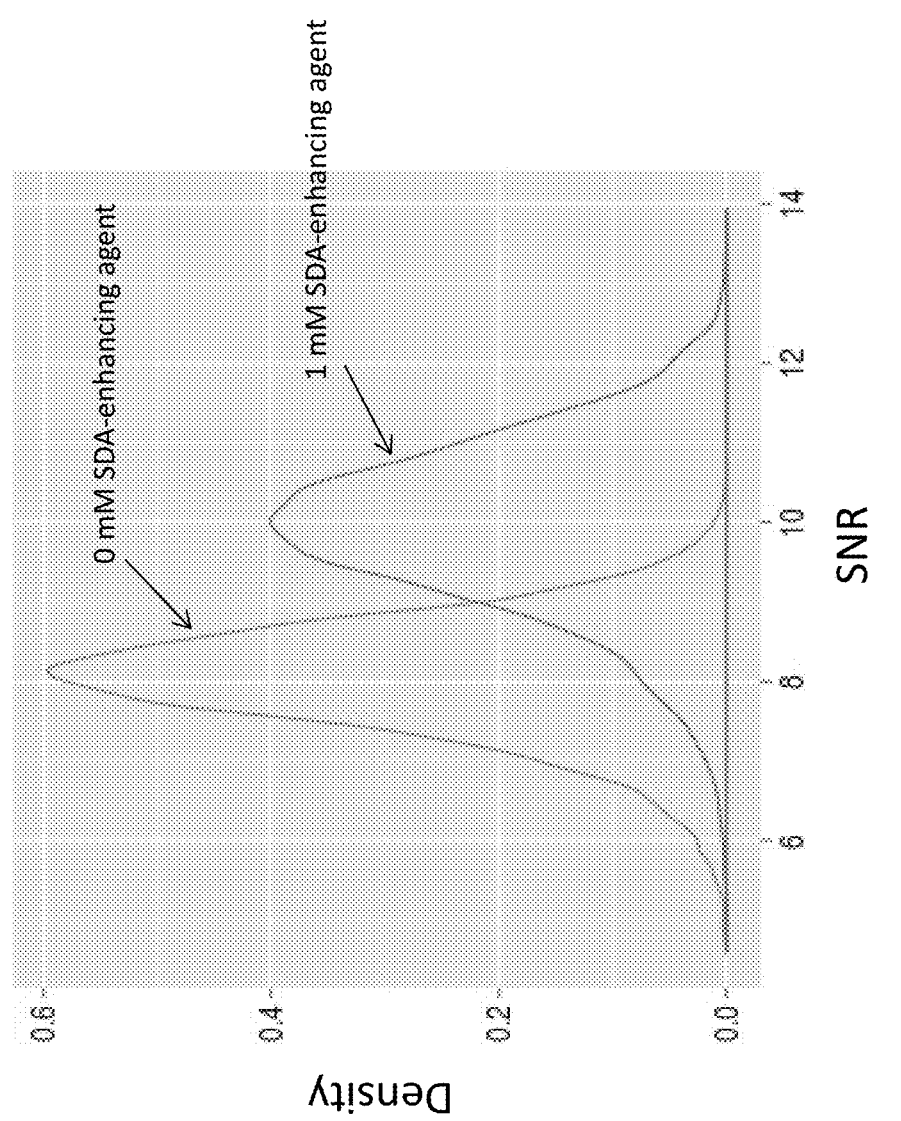
FIG. 2 is a graph illustrating an increase in SNR in the presence of an SDA-enhancing agent (no. 1 from Table 1) as compared to that for a reaction lacking the SDA-enhancing agent.
Figure 3:
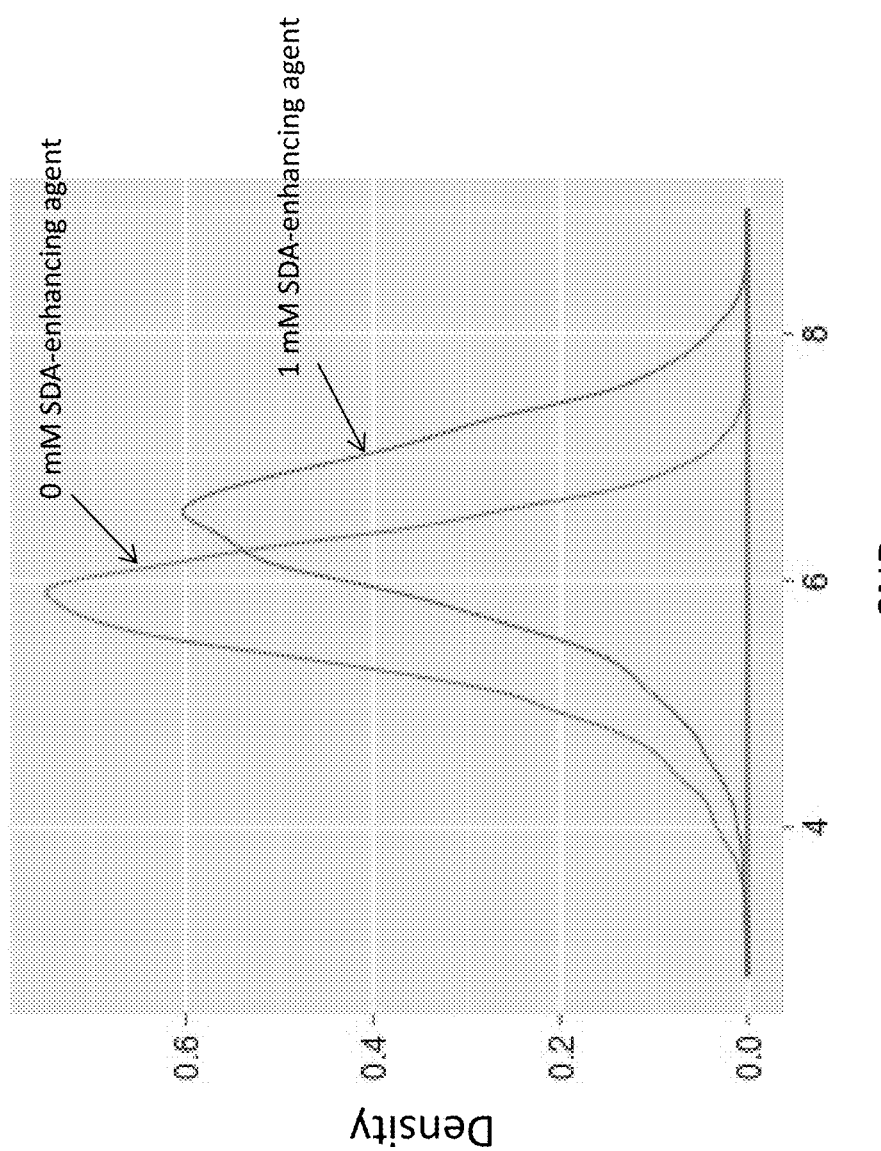
FIG. 3 is a graph illustrating an increase in SNR in the presence of an SDA-enhancing agent (no. 1 from Table 1) as compared to that for a reaction lacking the SDA-enhancing agent.
Figure 4:
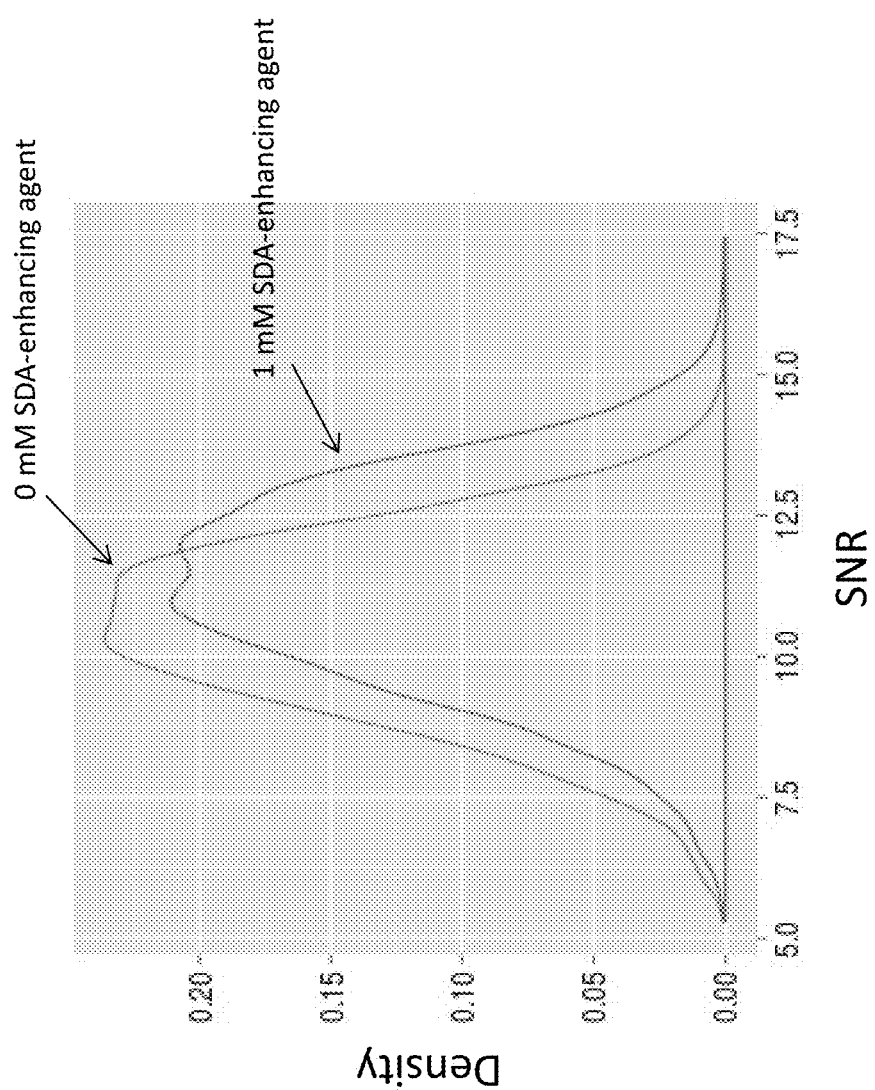
FIG. 4 is a graph illustrating an increase in SNR in the presence of an SDA-enhancing agent (no. 1 from Table 1) as compared to that for a reaction lacking the SDA-enhancing agent.

Example 1: SDA-Enhancing Agent Having Both SNR-Increasing Activity and Photoprotective Activity FIGS. 2 to 4 show the difference in SNR between a sequencing reaction comprising SDA-enhancing agent no. 1 from Table 1 and an identical sequencing reaction that lacks the SDA-enhancing agent. The formula of the SDA-enhancing agent no. 1 is as follows:

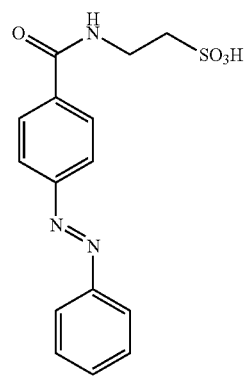 [SMILES: O=C(NCCS(=O)(=O)O)c1ccc(/N=N/c2ccccc2)cc1]

The fluorophore used for this SNR graph in FIG. 2 was a Cy3.5-dT. An approximately 25% increase in SNR was observed. FIG. 3 shows results for Cy3.5-dG, showing an approximately 14% increase in SNR in the presence of this SDA-enhancing agent. FIG. 4 provides SNR gain data for Cy5-dC in the sequencing reaction, showing a 1-2% increase in SNR.

Figure 5:
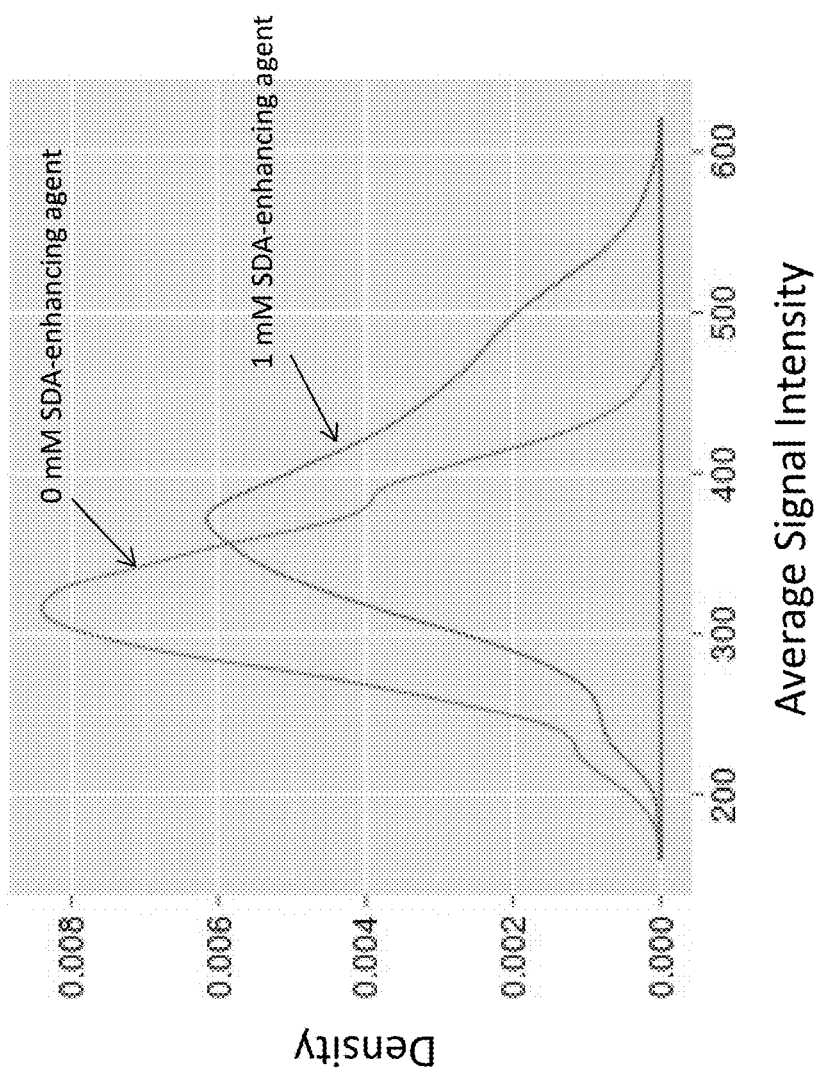
FIG. 5 is a graph showing the increase in intensity of signal in the presence of an SDA-enhancing agent (no. 1 from Table 1).

FIG. 5 is a graph showing the increase in intensity of signal for a Cy3.5-dT in the presence of SDA-enhancing agent no. 1, the brightness of the signal being increased by about 15%.

Figure 6:
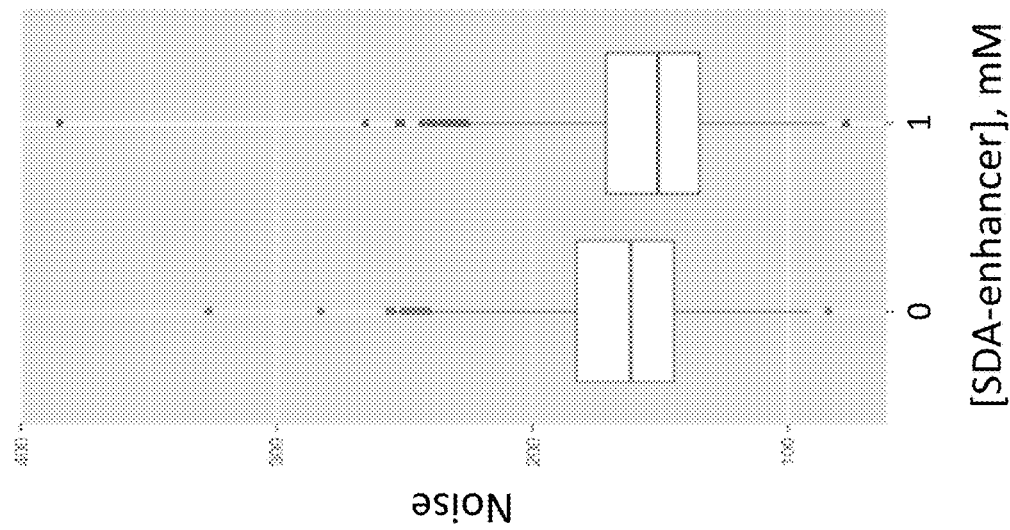
FIG. 6 provides data showing a reduction in noise in an experiment comprising an SDA-enhancing agent (no. 1 from Table 1).
Figure 7:
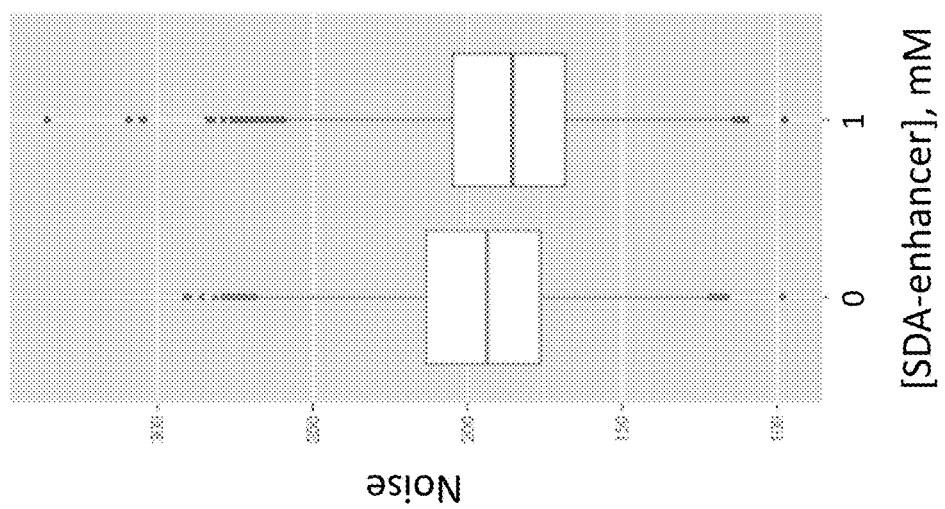
FIG. 7 provides data showing a reduction in noise in an experiment comprising an SDA-enhancing agent (no. 1 from Table 1).

FIG. 6 provides data showing an approximately 10% reduction in noise from Cy5-dC when SDA-enhancing agent no. 1 is present. Likewise, FIG. 7 shows a similar decrease in noise from Cy3.5-dT in the presence of this SDA-enhancing agent.

Figure 8:
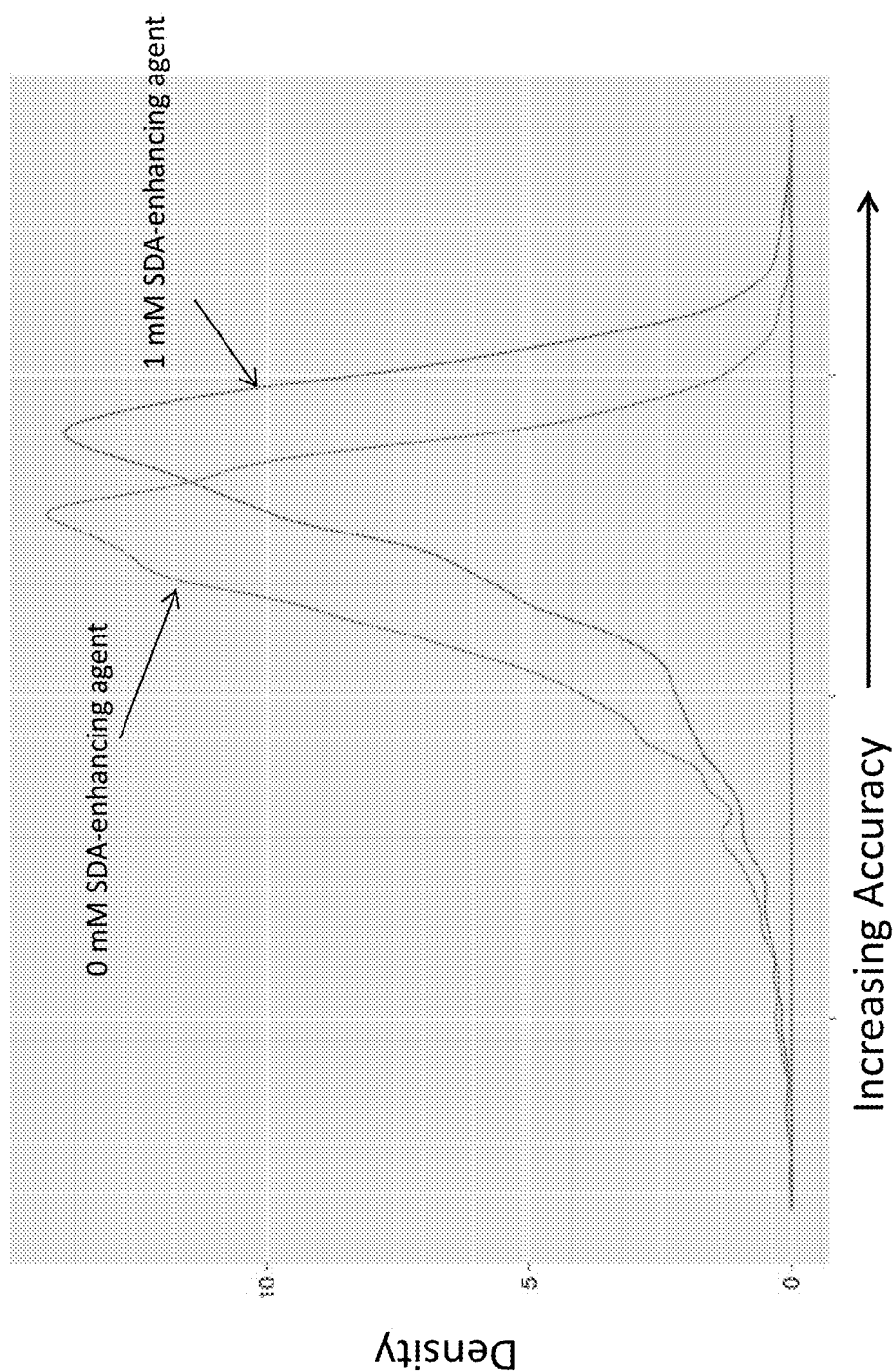
FIG. 8 shows the overall accuracy metric for sequencing reads from a sequencing reaction comprising multiple different fluorescent dyes in the absence and presence of an SDA-enhancing agent (no. 1 from Table 1).

This SDA-enhancing agent was also shown to increase overall accuracy of the sequencing reads. FIG. 8 shows the overall accuracy metric for sequencing reads from a sequencing reaction comprising deoxynucleotides labeled with different types of fluorescent dyes (a different dye on each different nucleotide) in the absence and presence of SDA-enhancing agent no. 1. This SDA-enhancing agent increased the accuracy of the sequencing data by approximately 2-3%, which is a very significant increase for single-molecule sequencing reactions.

In a series of follow up experiments, SNR-increasing activity of this SDA-enhancing agent was assessed further. Titration experiments showed that the SNR-increasing activity of the agent was effective from 100 µM to 1 mM in the sequencing reaction and did not show negative effects on the kinetics of the sequencing reaction in that broad range.

SDA-enhancing agent no. 1 was then tested in sequencing reactions in the presence of a triplet-state quencher (TSQ) that had previously been shown to have photoprotective activity (see U.S. Pat. No. 8,834,847 for a detailed description of this photoprotective molecule):

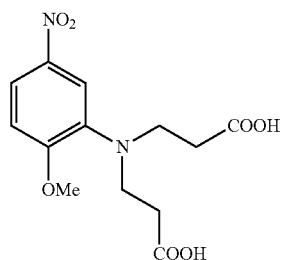 [SMILES: COc1ccc([N+](=O)[O-])cc1N(CCC(=O)O)CCC(=O)O]

Sequencing reactions were performed as described above in the presence of SDA-enhancing agent no. 1 at 300 µM, 600 µM, and 900 µM with titrated amounts of TSQ at 0 µM, 300 µM, 600 µM, and 900 µM (thus, a total of 12 reactions were performed). We unexpectedly found that including this SDA enhancing agent alone increased the accuracy of the sequencing reaction (i.e., over control reactions with no additive) as much as sequencing reactions with both DQ123 and the TSQ (data not shown). This experiment shows that in addition to its SNR-increasing activity, DQ-123 also has photoprotective activity. Thus, the addition of another photoprotective agent (e.g., TSQ) to reactions containing an SDA-enhancing agent is not needed.

Example 2: Testing of SDA-Enhancing Activity of Additional Compounds

Additional compounds were tested for SDA-enhancing activity in sequencing reactions performed as described above. Table 2 below shows the relative improvement in accuracy of the results of the sequencing reactions in the presence of the indicated amount of each compound. As indicated above, improvements in SNR and increased photoprotective effects in SMRT® sequencing reactions result in improvements in sequencing accuracy (i.e., the accuracy of a single sequencing pass through a template molecule for which the sequence is known). DQ-123 is provided as a positive control and a reaction without any SDA-enhancing agent is provided as negative control. Accuracies are provided relative to the negative control. These reactions did not contain any additional SNR-increasing or photoprotective compounds.

TABLE 2

| Relative Sequencing Accuracy in the Presence of SDA-enhancing Agents | |
|---|---|
| SDA-enhancing agent No. | Relative Accuracy[1] |
| No Agent | 0.86 |
| 1 | 1.00 |
| 2 | 1.00 |
| 3 | 1.00 |
| 4 | 1.00 |
| 5 | 1.00 |
| 6 | 1.00 |
| 7 | 1.00 |
| 8 | 1.00 |
| 9 | 1.00 |
| 10 | 1.00 |
| 11 | 0.99 |
| 12 | 0.99 |
| 13 | 0.99 |
| 14 | 0.99 |
| 15 | 0.99 |
| 16 | 0.98 |
| 17 | 0.98 |
| 18 | 0.98 |
| 29 | 0.98 |
| 20 | 0.97 |
| 21 | 0.97 |
| 22 | 0.97 |
| 23 | 0.97 |
| 24 | 0.96 |
| 25 | 0.96 |
| 26 | 0.94 |
| 27 | 0.93 |
| 28 | 0.93 |

[1]Accuracy relative to DQ123 accuracy performed in the same experiment.

As is clear from the table above, the inclusion of any one of compounds 1 to 28 in the sequencing reaction mixture improved its accuracy as compared to reactions with no SDA-enhancing agent (last row). Therefore, each of these compounds are included in the group of compounds described as SDA-enhancing agent of the invention herein.

What is claimed is:

1. A method for improving an illuminated sequencing reaction, the method comprising:
providing a sequencing reaction mixture comprising a polymerase, a template nucleic acid, and a fluorescent or fluorogenic nucleotide or nucleotide analog;
adding a signal detection assay (SDA)-enhancing agent to the sequencing reaction mixture, wherein the SDA-enhancing agent is selected from the group consisting of:

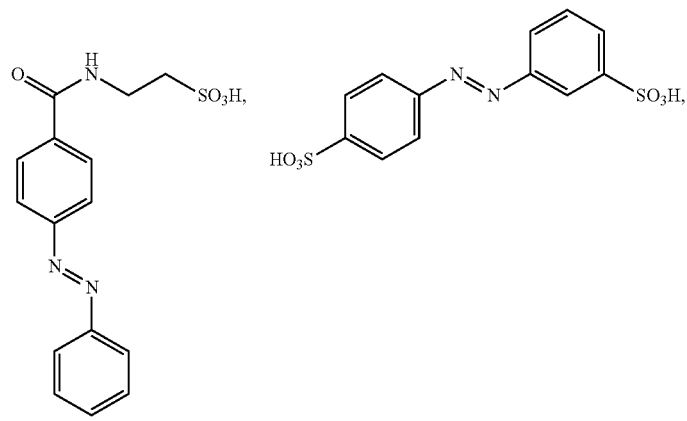
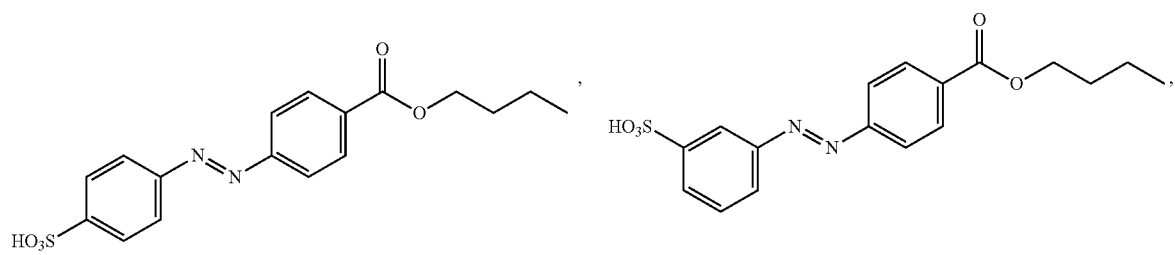
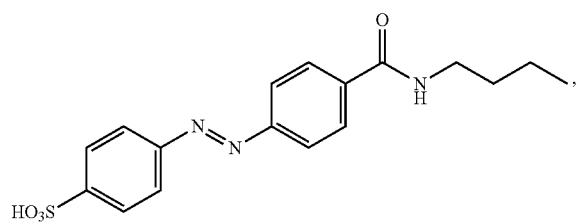
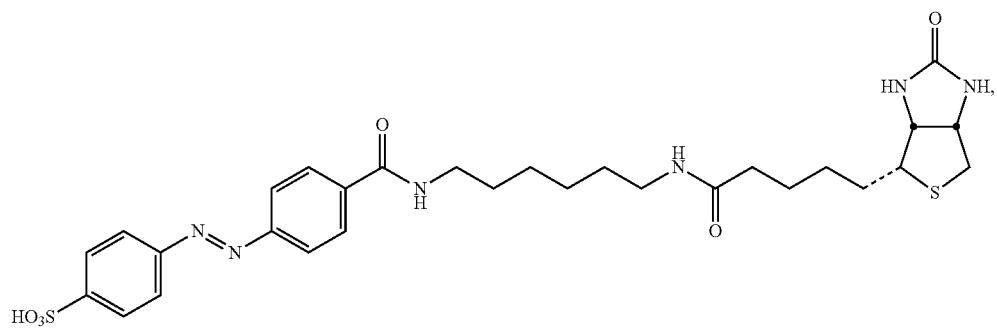
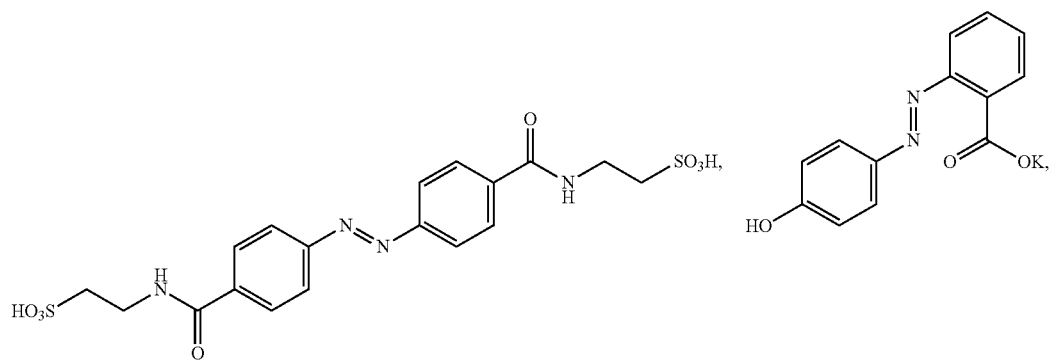

-continued
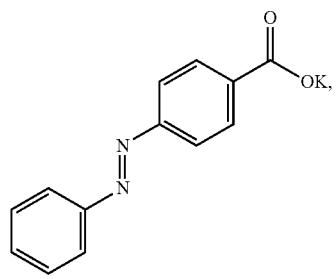
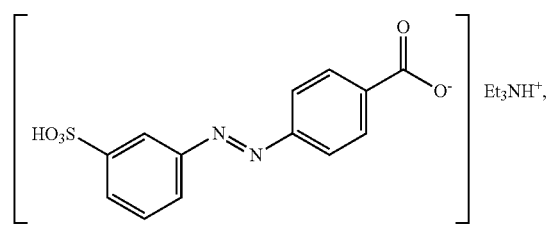
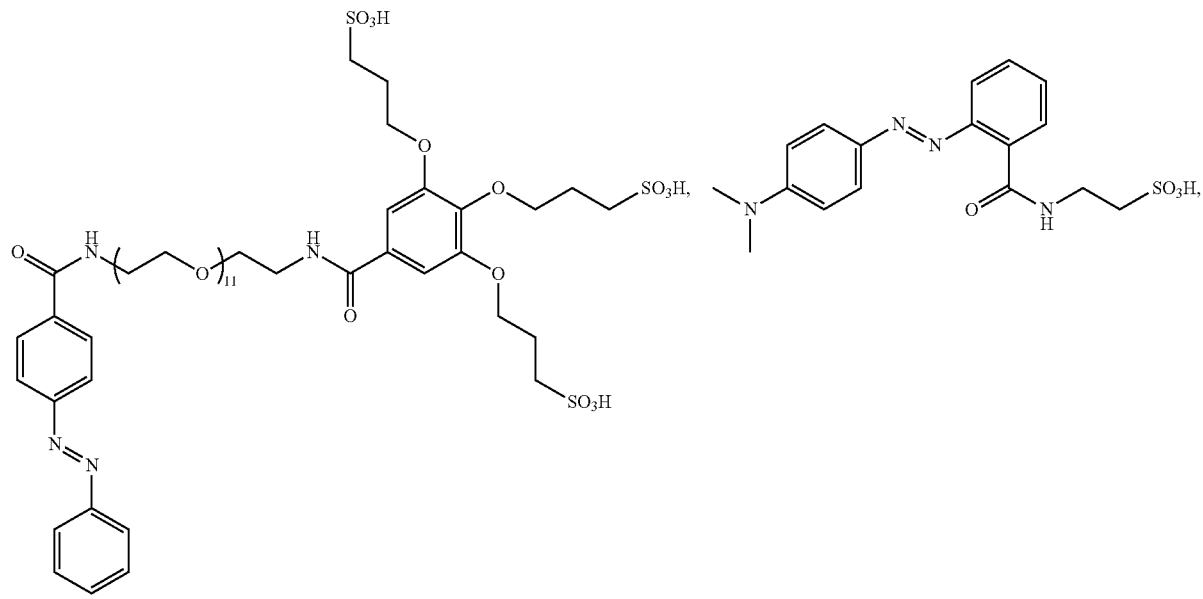
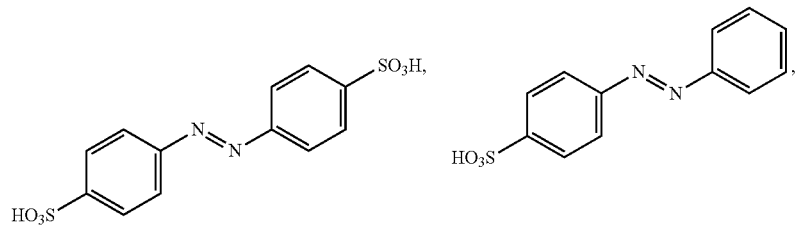
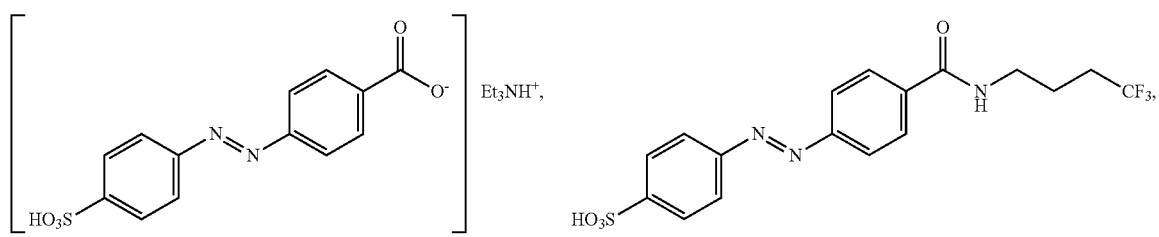
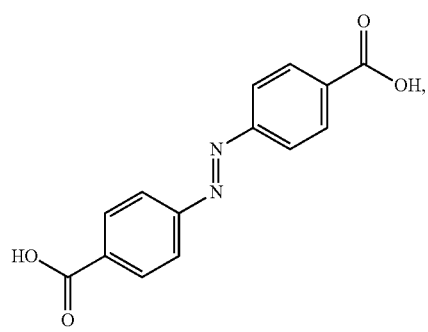

-continued
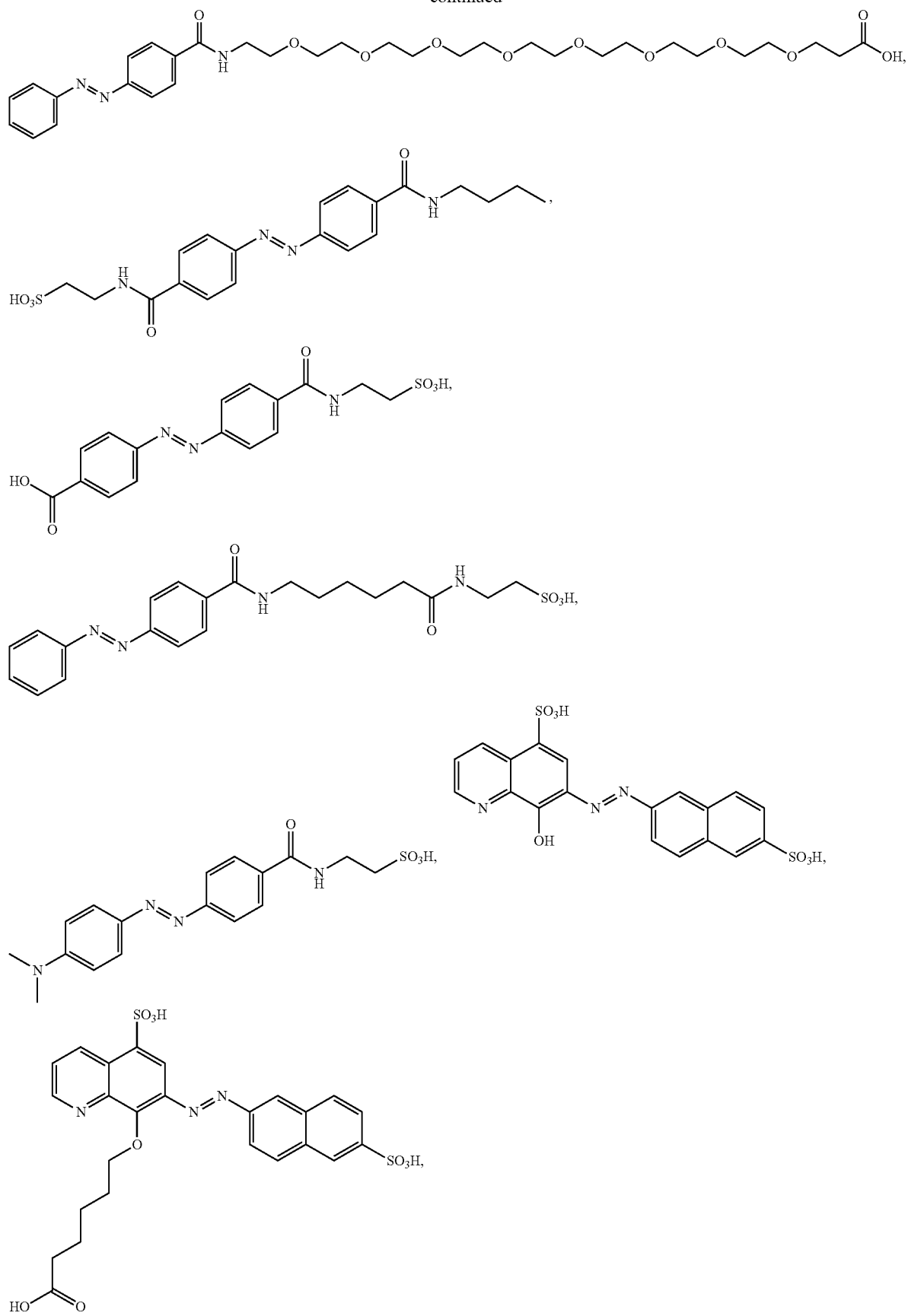

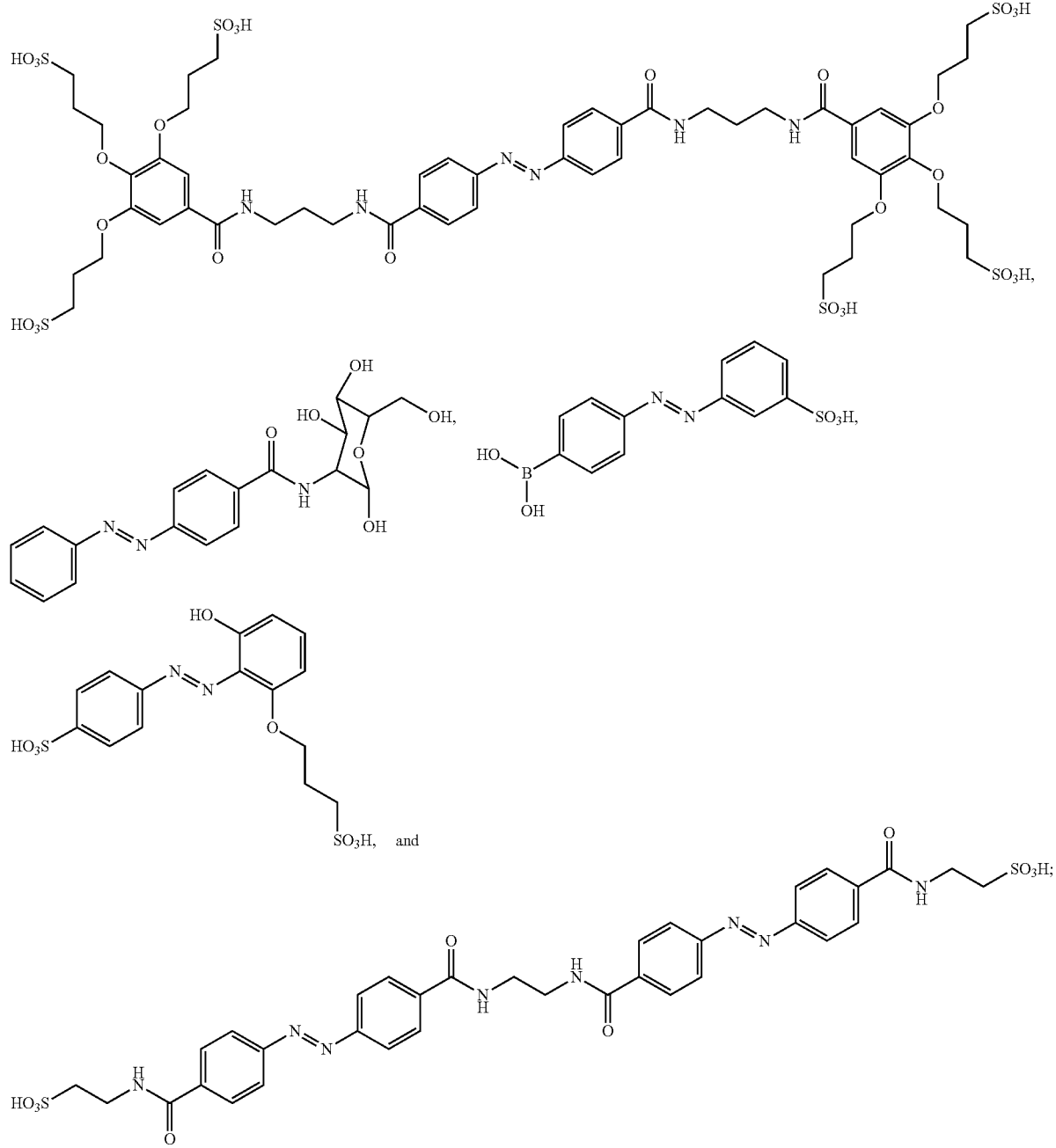

illuminating the sequencing reaction mixture with an excitation illumination; and monitoring a reaction between the polymerase, the template nucleic acid, and the fluorescent or fluorogenic nucleotide or nucleotide analog to detect an emission signal from the illuminated sequencing reaction mixture, wherein the SDA-enhancing agent results in an increased signal-to-noise ratio (SNR), enhanced photoprotection, or both, as compared to the illuminated sequencing reaction mixture in the absence of the SDA-enhancing agent.

2. The method of claim 1, wherein the polymerase is immobilized at a reaction site.

3. The method of claim 2, wherein said reaction site is within a zero-mode waveguide.

4. The method of claim 1, wherein said illuminated sequencing reaction is a base extension reaction.

5. The method of claim 1, wherein the SDA-enhancing agent resultsi n any one or any combination of: (i) an increased optical signal, (ii) a reduction in background noise, (iii) mitigation of photoinduced damage (PID) to the polymerase, and (iv) a reduction in blinking or photobleaching of the fluorescent or fluorogenic nucleotide or nucleotide analog, wherein (i) to (iv) are as compared to the illuminated sequencing reaction mixture in the absence of the SDA-enhancing agent.

6. The method of claim 1, wherein the SDA-enahcing agent results in both increased SNR and enhanced photoprotection as compared to the illuminated sequencing reaction mixture in the absence of the SDA-enhancing agent.

7. The method of claim 1, wherein the accuracy of the sequencing reaction is increased as compared to the illuminated sequencing reaction in the absence of the SDA-enhancing agent.

8. The method of claim 1, wherein the SDA-enhancing agent is:

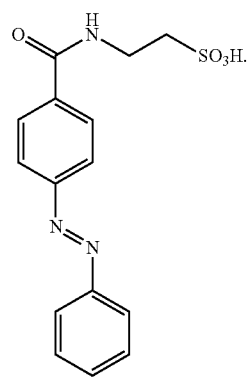 [SMILES: O=C(NCCS(=O)(=O)O)c1ccc(/N=N/c2ccccc2)cc1]

9. The method of claim 1, wherein the SDA-enhancing agent is:

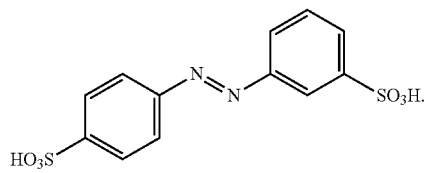 [SMILES: O=S(=O)(O)c1ccc(/N=N/c2cccc(S(=O)(=O)O)c2)cc1]

10. The method of claim 1, wherein the SDA-enhancing agent is:

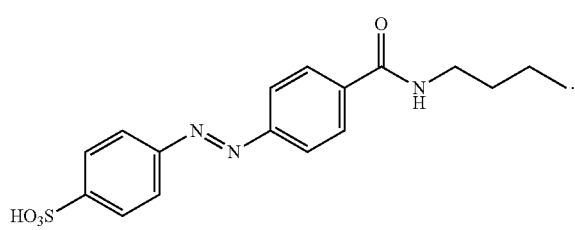 [SMILES: CCCCNC(=O)c1ccc(/N=N/c2ccc(S(=O)(=O)O)cc2)cc1]

11. The method of claim 1, wherein the SDA-enhancing agent is:

12. The method of claim 1, wherein the SDA-enhancing agent is:

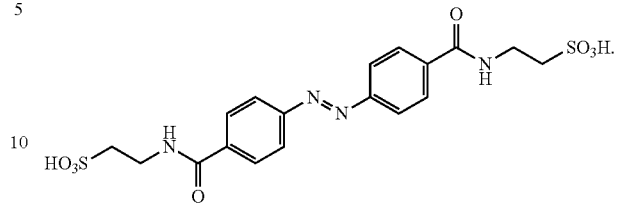

13. The method of claim 1, wherein the SDA-enhancing agent is:

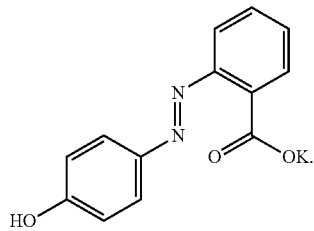

14. The method of claim 1, wherein the SDA-enhancing agent is:

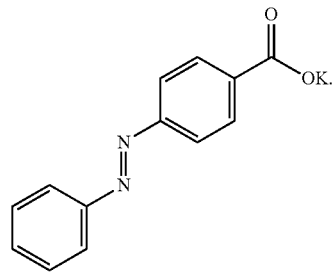

15. The method of claim 1, wherein the SDA-enhancing agent is:

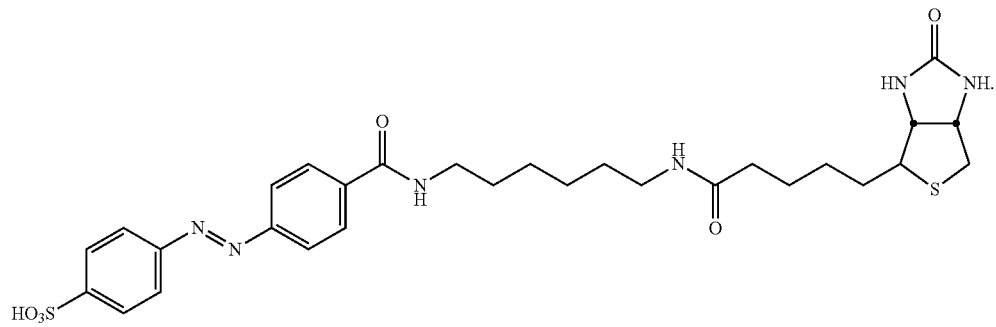

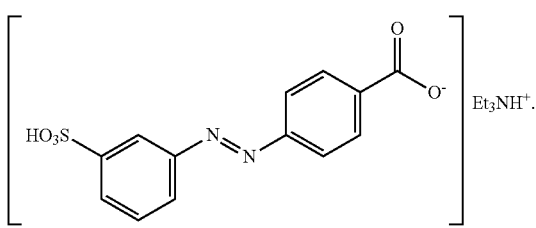
16. The method of claim 1, wherein the SDA-enhancing agent is:
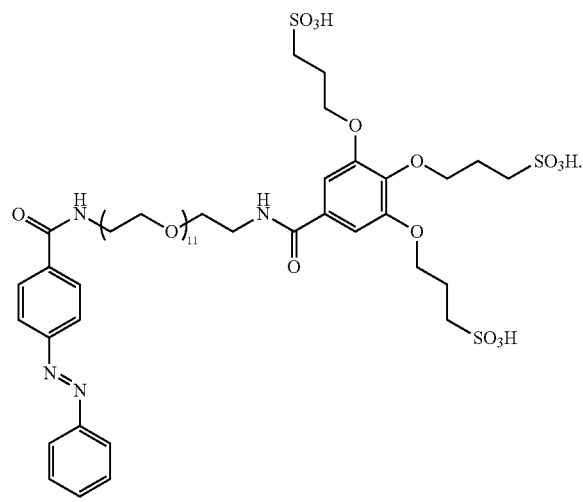
17. The method of claim 1, wherein the SDA-enhancing agent is:
18. The method of claim 1, wherein the SDA-enahcing agent is:
\* \* \* \* \*